United States Patent
Deckert et al.

(10) Patent No.: US 6,203,528 B1
(45) Date of Patent: Mar. 20, 2001

(54) UNITARY MOLDED ELASTOMER CONDUIT FOR USE WITH A MEDICAL INFUSION PUMP

(75) Inventors: Clinton L. Deckert, Poway, CA (US); James T. Maerzke, Kenosha, WI (US); Jeffrey P. Brown, Danville, VA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/281,236

(22) Filed: Mar. 30, 1999

Related U.S. Application Data

(63) Continuation-in-part of application No. 08/398,886, filed on Mar. 6, 1995, now Pat. No. 5,904,668.

(51) Int. Cl.$^7$ .................................................. A61M 37/00
(52) U.S. Cl. ............................................ 604/131; 604/153
(58) Field of Search ................................... 604/30, 31, 32, 604/33, 34, 65, 66, 67, 131, 153; 417/474, 477.1, 477.2, 477.3, 477.5

(56) References Cited

U.S. PATENT DOCUMENTS

| | | |
|---|---|---|
| 3,848,634 | 11/1974 | Noiles . |
| 5,205,153 | 4/1993 | Hlavinka et al. . |

FOREIGN PATENT DOCUMENTS

| | | |
|---|---|---|
| 0 524 605 A1 | 1/1993 | (EP) . |
| 2 207 902 | 2/1989 | (GB) . |

*Primary Examiner*—Manuel Mendez
(74) *Attorney, Agent, or Firm*—Wallenstein & Wagner

(57) ABSTRACT

A unitary molded elastomer conduit for use with a medical infusion pump. The molded conduit includes a plurality of elongated tubular sections defining a continuous lumen therethrough. A first interior surface of the molded conduit includes an interior region having surface characteristics for clamping off the lumen to stop the flow of fluid transport, or for clamping the lumen for use with the peristaltic mechanism of the medical infusion pump. Another interior surface is provided in the molded conduit which is associated with another of the plurality of elongated sections of the integral elastomer conduit. The second interior surface defines a second interior region having surface characteristics for coupling ultrasound across the conduit traversed to the lumen in order to detect gas entrainment and the like. The second interior region thus provides a textured surface relative to the first interior region to direct the signal energy from the signal coupled across the conduit traversed to the lumen. Additionally, external features may be provided for positioning the plurality of elongated tubular sections of the conduit relative to the peristaltic pumping mechanism of the medical infusion pump for fluid transport and characterization.

30 Claims, 14 Drawing Sheets

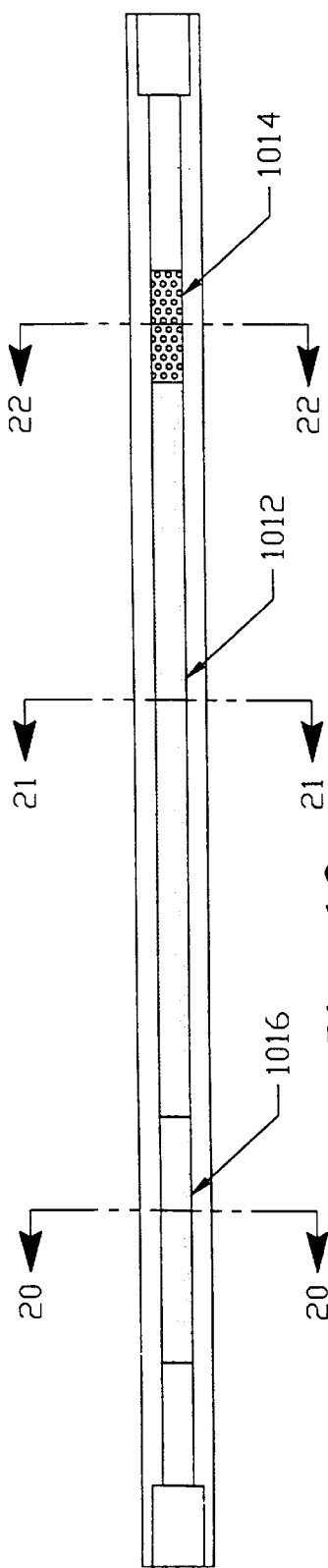
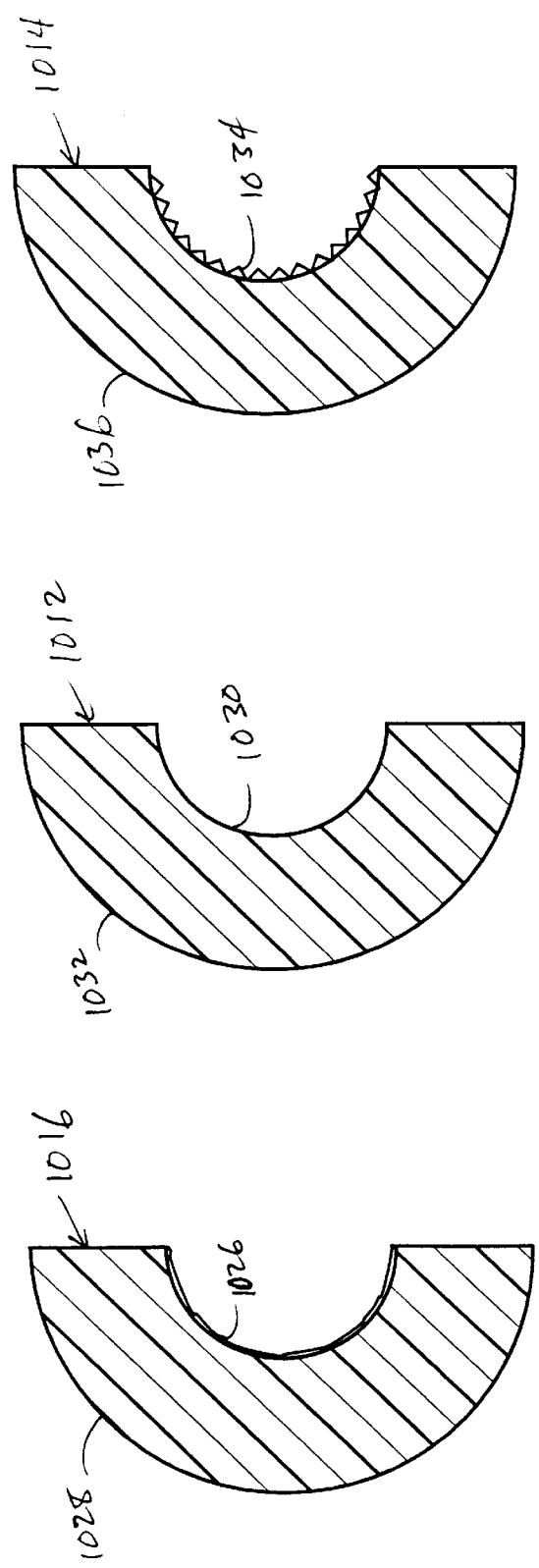
Fig. 19  Fig. 20  Fig. 21  Fig. 22

UNITARY MOLDED ELASTOMER CONDUIT FOR USE WITH A MEDICAL INFUSION PUMP

CROSS-REFERENCE TO RELATED APPLICATIONS

This is a continuation-in-part of U.S. application Ser. No. 08/398,886, filed Mar. 6, 1995 now U.S. Pat. No. 5,904,668.

BACKGROUND OF THE INVENTION

1. Field of the Invention

The present invention is directed to a cassette for an infusion pump which may be inserted into and removed from the pump. More particularly, the present invention relates to an infusion pump cassette having a unitary injection molded elastomer conduit for fluid transport with a medical infusion pump.

2. Background and Description of Related Art

An infusion pump is used to automatically administer liquid medicant to a patient. The liquid medicant is supplied from a source of medicant and pumped into the patient via a catheter or other injection device. The manner in which the liquid is infused is controlled by the infusion pump, which may have various modes of infusion, such as a continuous mode in which the liquid medicant is continuously infused at a constant rate; or a ramp mode in which the rate of infusion gradually increases, then remains constant, and then gradually decreases. With the cost savings that may be attained today using home health care, small portable medical infusion pumps have become common for use in home treatment to provide for instance chemotherapy, pain management, and the like. These treatments often require the controlled infusion regimens discussed herein.

Portable medical infusion pumps typically run open loop for displacing a volume of medicament fluids with the peristaltic pumping mechanism of the medical infusion pump. The pump chamber of the infusion pump cassette displaces predetermined amounts of the medicament fluids infused with the stroke volume defined by the elongated tubular sections of the fluid transport swept through the conduit of the pump cassette which supports the elongated conduit. Thus, volumetric flow rate is determined in part by the controlled dimensional tolerances of the elongated tubular section inner diameter and length. A cassette utilized by the infusion pump is typically disposable, and thus must be manufactured in a cost effective manner, while requiring consistent cassette operation defined through the dimensional tolerances of the pump chamber provided by the cassette assembly.

Drugs being used with home therapy are increasingly becoming expensive for such things as therapies that may be involved in treatment of pulmonary hypertension, chemotherapy, and the like. Additionally, keep vein open (KVO) applications require replenishing of the liquid medicament supply periodically by a nurse or other medical professional which may from time to time visit the patient at home. It is important, therefore, to be able to know with a degree of certainty that the medicament is being delivered to the patient within a narrow therapeutic range for effective treatment for patients on closely monitored treatments. Also, where the medications are costly, it would be advantageous to be assured that the leftover drugs of the medicament bags are minimal to avoid waste, since after they are used in treatment, these drugs must be discarded and cannot be recycled for later use.

Additionally, the medicament liquid should not become depleted prior to the arrival of medical personnel for replacing the regimen. In the case of a KVO application, premature termination of the application may result in clotted access devices which are blocked by blood clots requiring considerable additional effort by the medical personnel responsible for the home therapy. Thus, it is important to maintain tight tolerances for and improve the accuracy of such portable medical infusion pump equipment.

One such cassette or module which may be inserted into and removed from the pump, is disclosed in U.S. Pat. No. 5,257,978 to Haber et al. A module disclosed by Haber et al. receives a length of an intravenous line in its interior, and a length of silicone tubing is connected to the intravenous line to form a single continuous conduit. The module is insertable into an infusion pump, in the form of a peristaltic pump, via a door which may be opened and closed. The Haber et al. pump is constructed so that it will operate only when the door is completely closed.

Additionally, U.S. Pat. No. 5,551,850 to Williamson et al. discloses the use of an elastomeric conduit used in the pump chamber, which is intended to result in a uniform pump chamber discharge volume by using materials of a relating constant storage modulus or stiffness. The Williamson et al. pump chamber assembly includes a pump chamber made of polyurethane tubing which was selected for the pump chamber because of its ability to rebound and its stiffness creating a hydraulically rigid section that resists volume changes due to system pressure variances.

The pump chamber assembly also includes inlet and outlet valve tubes coupled to the pump chamber, and inlet and outlet clips separate from the pump chamber and valve tube for securing the pump chamber to the cassette module of the infusion pump. Williamson et al. teach the use of particular materials not only for their mechanical properties, but also for the ability to solvent bond the component materials to other component materials of the assembly. Although Williamson et al. acknowledge that silicone has desirable features, including a relatively constant storage modulus or stiffness and a relatively low dynamic mechanical analysis tangent versus temperature over a range of operating temperatures, however, the silicone is considered to be difficult to solvent bond to other materials and therefore not suitable in a multicomponent solution. The use of solvent bonded materials in the pump chamber however adds cost to the manufacture and increases the difficulty of assembly of the pump chamber for use in the medical infusion pump cassette module, as well as, creating the possibility for malfunction due to failure of the solvent bond between materials. Therefore, it would be desirable to provide a unitary molded elastomer conduit for use with the pump chamber of the infusion pump cassette module, which improves the manufacturability and reliability, as well as the cost of the overall medical infusion pump system.

SUMMARY OF THE INVENTION

A cassette adapted to be insertable into and removable from an infusion pump has a housing carrying a flexible tubing. The flexible tubing includes a unitary elastomer conduit such as a pyrogen free silicone. The flexible tubing is provided as a molded elastomer conduit having integral elongated tubular sections. The molded elastomer conduit is received by the cassette assembly for use with the medical infusion pump. The unitary molded elastomer provides for a single pump chamber component which simplifies the manufacture of the cassette module, while at the same time tight dimensional tolerances can be maintained through the molding process. To this end, the molding of the elastomer conduit provides more consistent manufacture and tighter tolerances than may be achieved through the extrusion of elastomer tubing for use as a component part of the pump chamber of the medical infusion pump. The molding process also facilitates the use of one or more external features such as alignment tabs on the outside of the conduit for positioning of the conduit in the cassette. In the described embodiments, the mold also provides for predetermined surface characteristics which enhance the overall medical pump operation by smoothing or narrowing of interior and exterior surfaces and defined surface features of the elastomer conduit to facilitate alignment of the tube in the cassette, clamping off of the lumen defined by the conduit, for coupling ultrasonic energy across the conduit such as ultrasonic waves used for characterization of the fluid transport such as air-in-line detection and the like.

Briefly summarized, the present invention relates to a unitary molded elastomer conduit for use with a medical infusion pump. The molded conduit includes a plurality of elongated tubular sections defining a continuous lumen therethrough. A first interior surface of the molded conduit is associated with one of the plurality of elongated tubular sections, and includes a first interior region having surface characteristics for clamping off the lumen to stop the flow of fluid transport, or for clamping the lumen for use with the peristaltic mechanism of the medical infusion pump. A second interior surface is provided in the molded conduit which is associated with another of the plurality of elongated sections of the integral elastomer conduit. The second interior surface provides a second interior region having surface characteristics for effectively coupling a signal such as an ultrasonic energy across the conduit traversed to the lumen in such a manner that the discrimination of air entrainment in the conduit and medicament is enhanced. The second interior region thus provides a textured surface relative to the first interior region to couple the signal energy across the conduit traversed to the lumen. Additionally, external features may be provided for positioning the plurality of elongated tubular sections of the conduit relative to the peristaltic pumping mechanism of the medical infusion pump for fluid transport and characterization.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIGS. 18 and 19 illustrate the plurality of elongated tubular sections defining a continuous lumen to the unitary molded elastomer conduit showing the various regions of the conduit for use with the medical infusion pump; and FIGS. 20, 21, and 22 are cross-sectional views of the elastomer conduit of FIG. 19 illustrating the interior surfaces of the conduit associated with a plurality of the elongated tubular sections of the conduit.

DETAILED DESCRIPTION OF THE PREFERRED EMBODIMENTS

Figure 1:
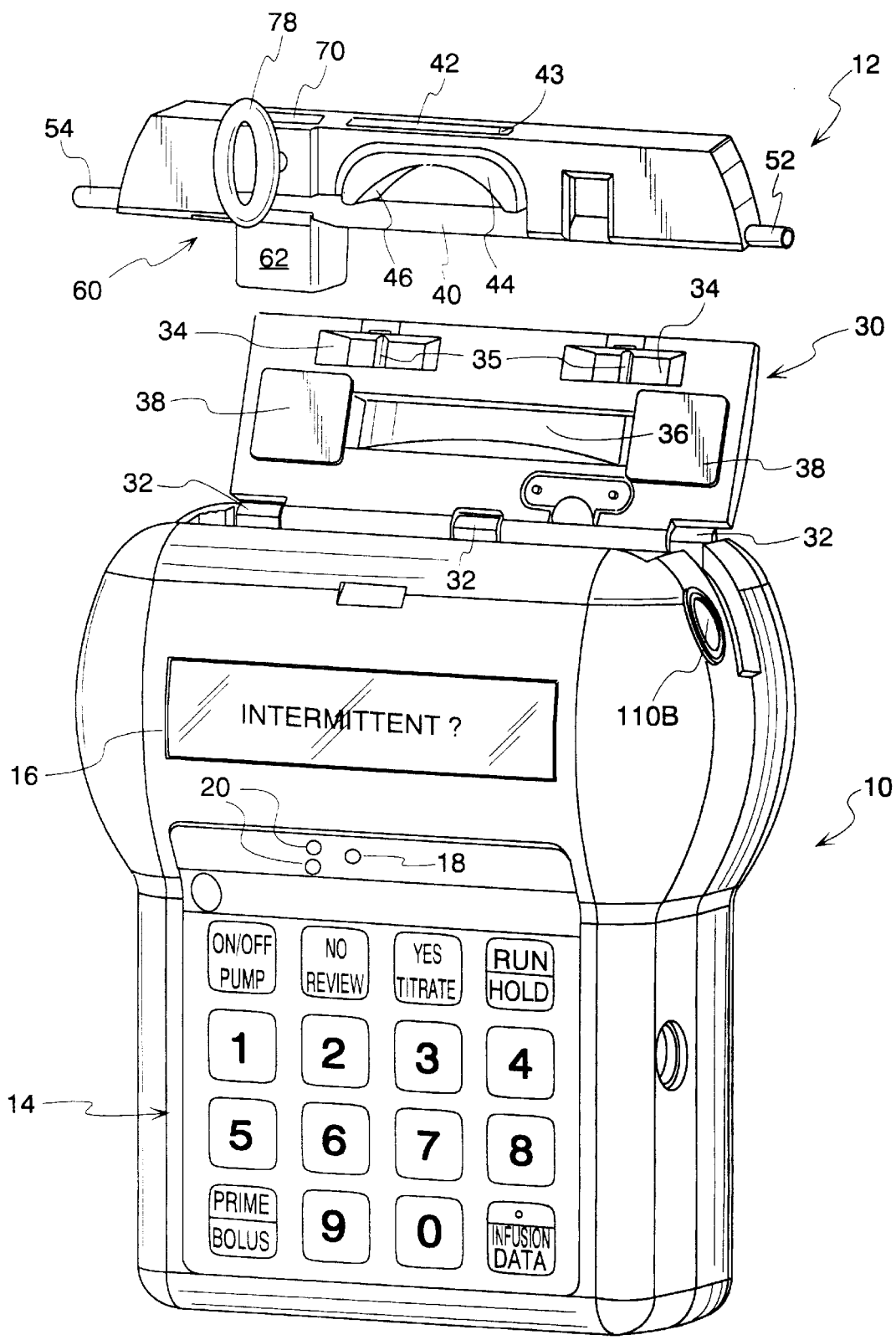
FIG. 1 is a perspective view of an ambulatory infusion pump and a first type of cassette which is insertable into the pump.

A preferred embodiment of a battery-powered, ambulatory infusion pump 10 in accordance with the invention is illustrated in FIG. 1 along with a first type of cassette 12 which is insertable into the pump 10. The portable pump 10 may be carried in a pouch or other device (not shown) attached to a patient so that the pump 10 may be carried wherever the patient goes.

The infusion pump 10 has a keypad 14 via which a user may input data and commands, a selectively back-lighted, dot matrix display 16 for displaying textual messages to the user, a light sensor 18 for detecting the level of ambient light, and a pair of light-emitting diodes (LED) 20, a green LED for indicating the normal operation of the pump 10 and a red LED for indicating an alarm or abnormal operating condition of the pump 10. As described below, the level of the light sensed by the ambient light sensor 18 is used to control when the display 16 is backlighted.

A door 30 is pivotally attached to the upper portion of the infusion pump 10 via a number of hinges 32. The underside of the door 30, which is shown in FIG. 1, has a pair of slots formed therein in which a pair of metal rods 35 are fixed. As described below, each of the metal rods 35 selectively engages a pair of slidable latching members to retain the door 30 in the closed position during operation of the pump 10.

Figure 4A:
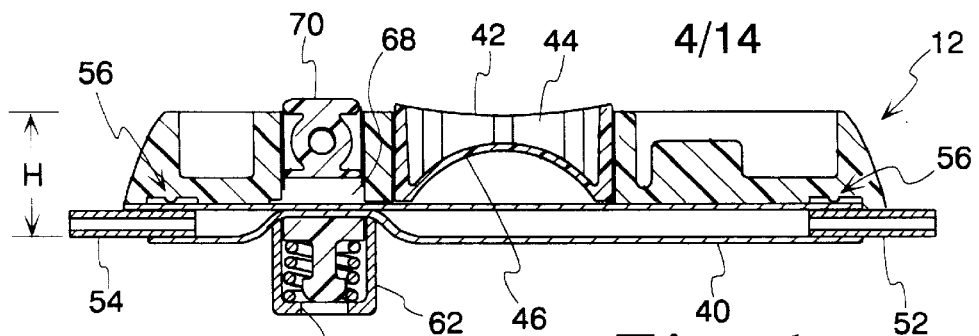
FIG. 4A is a cross-sectional side view of the first type of cassette in which a flexible tube is clamped.
Figure 4B:
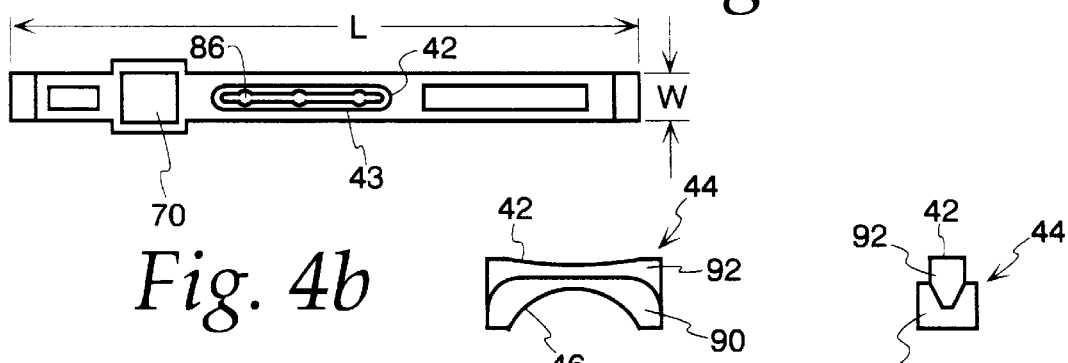
FIG. 4B is a top view of the cassette of FIG. 4A.

An arcuate metal leaf spring 36 is disposed on the underside of the door 30. The two ends of the leaf spring 36 are anchored by a pair of retaining elements 38 fixed to the door 30. When the cassette 12, in which a flexible silicone tube 40 is disposed, is inserted into the pump 10 and the door 30 is closed, the leaf spring 36 makes contact with and applies a downward force on the upper surface 42 of a vertically movable platen 44. As shown in FIGS. 1 and 4B, the upper surface 42 of the platen 44 is disposed within an elongated slot or aperture 43 disposed in the upper surface of the cassette housing 12. The platen 44 has a lower curved surface 46 against which the flexible tube 40 is pressed by a number of rollers 48 disposed on a conventional rotary pump wheel 49 (see FIG. 2A) to facilitate pumping of liquid through the tube 40. The rotary pump wheel 49 is fixed to a gear 50 (FIG. 2B) which is driven by a drive belt (not shown) connected to a DC motor 51 (FIG. 7) via a gear drive assembly (not shown).

Liquid is supplied to the tube 40 via a supply tube 52 connected to a source of liquid, which may be a liquid supply container or bag (not shown) fixed to the housing of the pump 10. The liquid is infused into the patient via a catheter or other injection device (not shown) fluidly connected to a length of tubing 54 fluidly connected to the tube 40. The tubing 52, 54 may comprise conventional polyvinylchloride (PVC) tubing having an outside diameter slightly larger than the inside diameter of the flexible tube 40 so that the tubing 52, 54 may be inserted into the flexible tube 40 to effect a liquid-tight seal.

The tubing 52, 54 may be solvent-bonded to the cassette housing 12, which is plastic, to prevent the tubing 52, 54 from being inadvertently pulled from the tube 40. As shown in FIG. 4A, the bottom portion of the cassette 12 has two semi-circular retaining members 56 integrally formed therewith, each of which abuts a portion of the flexible tube 40 where it overlaps the tubing 52, 54 to further prevent the tubing 52, 54 from being inadvertently pulled from the tube 40. A second pair of similar semi-circular retaining members are integrally formed with the pump housing at a point directly below the retaining members 56, as shown in FIGS. 2A and 3A, for the same purpose.

The cassette 12 has a flow-stop mechanism 60 that automatically clamps the flexible tube 40 shut when the cassette 12 is not disposed in the pump 10 or when the pump door 30 is open. The flow-stop mechanism 60, which is shown in detail in FIGS. 2A and 2B, has a housing 62 in which a vertically displaceable flow-stop member 64 and a spring 66 are disposed. As shown in FIG. 2B, the flexible tube 40 passes through a slot 68 formed in the flow-stop member 64, and the spring 66 biases the flow-stop member 64 upwardly.

While the cassette 12 is disposed in the pump 10 with the door 30 closed, one of the spring retaining members 38 makes contact with an upper surface 70 of the flow-stop member 64, thus preventing the spring 66 from forcing the flow-stop member 64 upwards enough to cause the flexible tube 40 to be flattened by the bottom surface of the slot 68. When the door 30 is opened, or when the cassette 12 is not disposed within the pump 10, the spring 66 forces the flow-stop member 64 upwards a distance sufficient to flatten the flexible tube 40, as shown in FIG. 4A, so as to prevent any liquid flow therethrough.

Figure 2A:
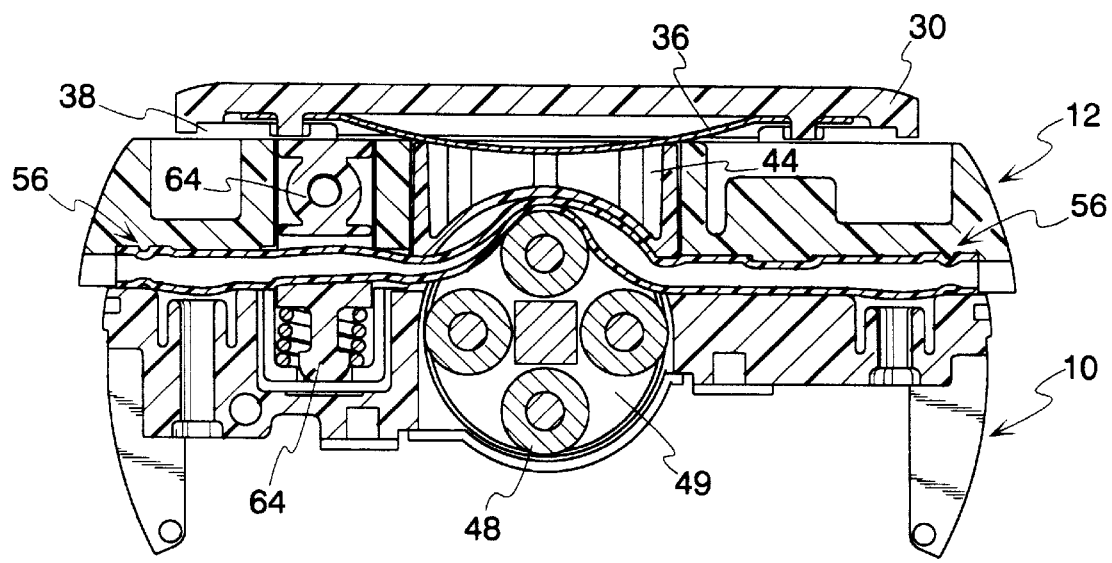
FIG. 2A is a cross-sectional front view of a portion of the infusion pump of FIG. 1 with the cassette disposed therein.
Figure 2B:
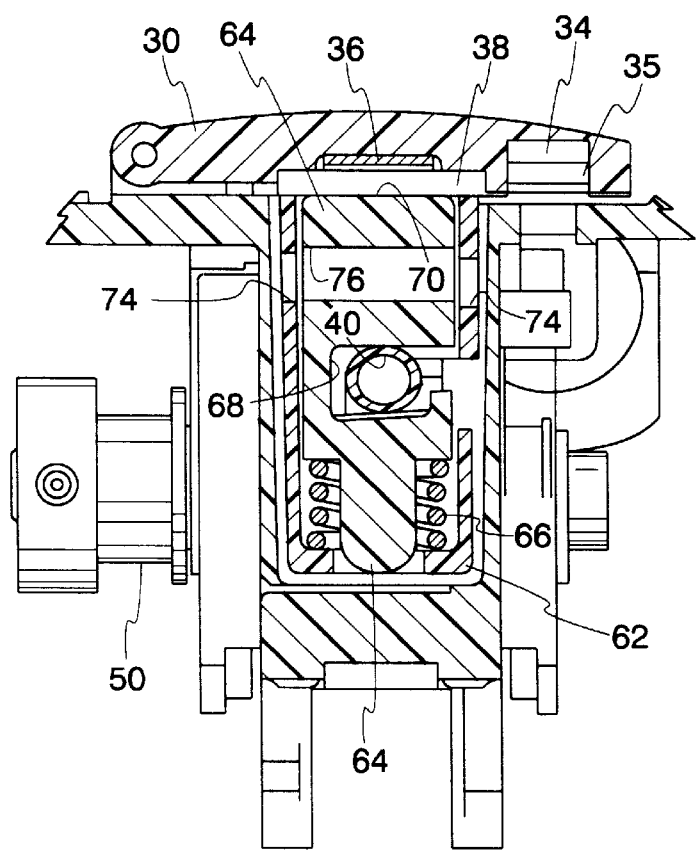
FIG. 2B is a cross-sectional side view of a portion of the infusion pump of FIG. 1 with the cassette disposed therein.
Figure 3A:
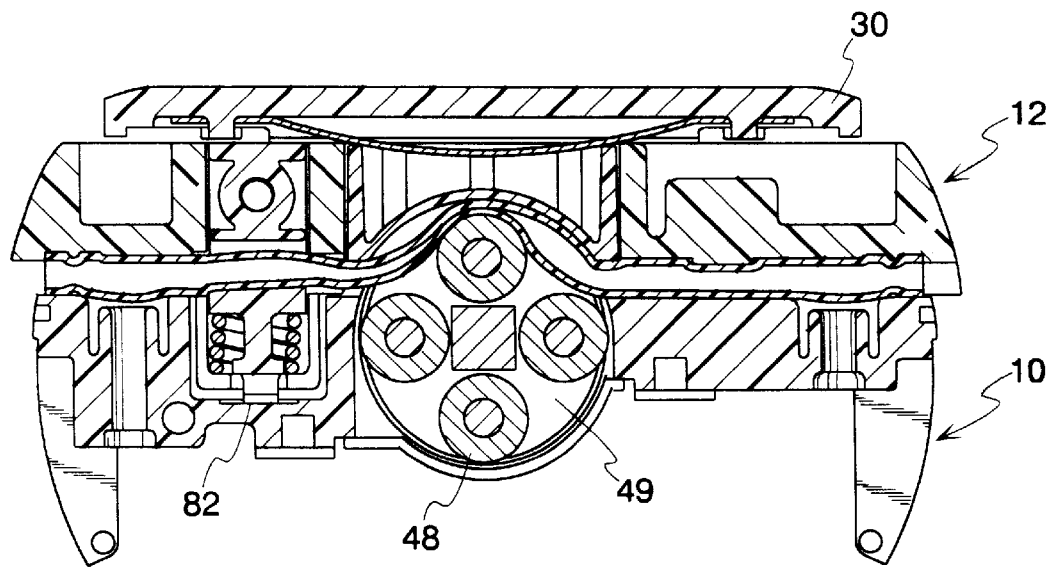
FIG. 3A is a cross-sectional front view of a portion of the infusion pump of FIG. 1 with a second type of cassette disposed therein.

When the cassette 12 is in the pump 10, as the pump door 30 is closed, one of the rollers 48 of the rotary pump wheel 49 will make contact with the flexible tube 40, causing it to be clamped shut, as shown in FIGS. 2A and 3A, and then subsequently, as the door 30 closes further, the flow stop member 64 will be forced downwards, unclamping the flexible tube 40. Thus, the tube 40 will be clamped at all times, either by one of the rollers 48 or by the flow stop member 64. Similarly, as the door 30 is opened, the flow stop member 64 will clamp the flexible tube 40 before the roller(s) 48 of the rotary pump wheel 49 unclamp the tube 40, thus preventing any liquid free-flow through the tube 40.

When the cassette 12 is not inserted into the pump 10, the flow-stop mechanism 60 may be disabled by manually aligning a bore 74 (FIG. 2B) in the flow-stop housing 62 with a bore 76 in the flow-stop member 64 and inserting a pin 78 (see FIG. 1) into the aligned bores 74, 76. When placed in the bores 74, 76, the pin 78 will prevent the flow-stop member 64 from being displaced upwardly by the spring 66, and thus prevent the flexible tube 44 from being flattened and the liquid flow from being cut off.

Figure 3B:
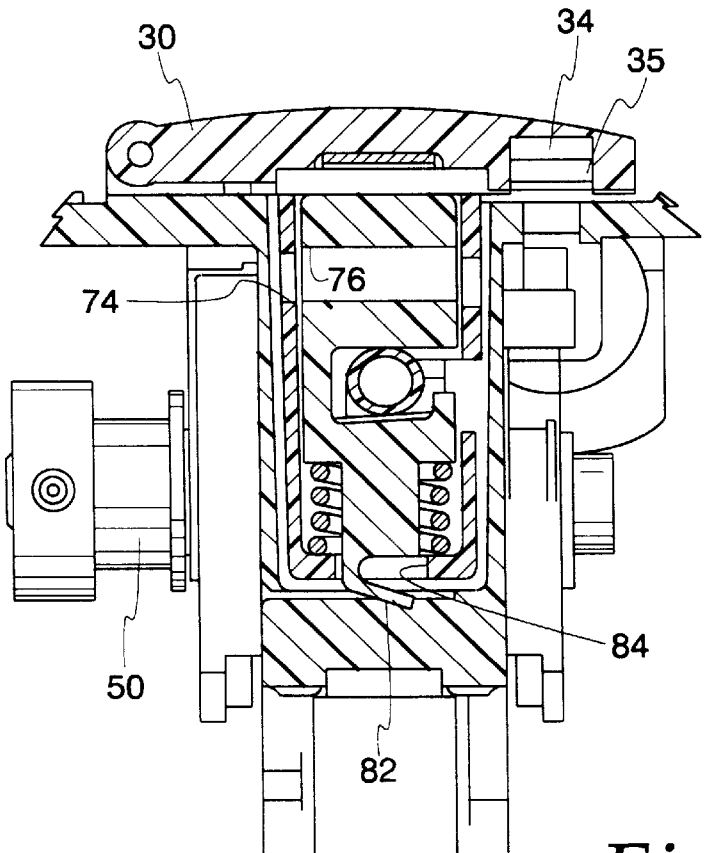
FIG. 3B is a cross-sectional side view of a portion of the infusion pump of FIG. 1 with the second type of cassette disposed therein.

FIGS. 3A and 3B illustrate a second type of cassette, which is shown disposed within the infusion pump 10. The only difference between the two types of cassettes 12 is the size and shape of the bottom portion of the flow-stop member 64. The bottom portion of the flow-stop member 64 of the first type of cassette 12, shown in FIGS. 2A and 2B, is generally spherical and does not extend outside of the flow-stop housing 62. The bottom portion of the flow-stop member 64 of the second type of cassette 12, shown in FIGS. 3A and 3B, has a downwardly angled finger 82 that extends through a circular bore 84 disposed in the bottom of the flow-stop housing 62.

Referring to FIGS. 4A and 4B, the cassette 12 has a length L of approximately 9.7 centimeters (cm), a height H of approximately 1.5 cm, and a width W of approximately 0.8 cm. The outer diameter of the flexible tube 40 (when undistorted) is approximately 0.4 cm.

Figure 5A:
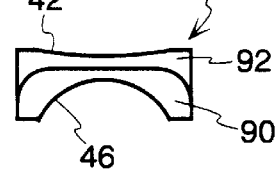
FIG. 5A is a front elevational view of a platen which forms part of the cassette of FIG. 4A.
Figure 5B:
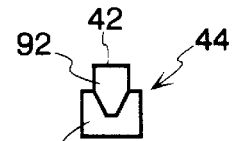
FIG. 5B is a side elevational view of the platen of FIG. 5A.

The upper surface 42 of the platen 44, which is shown in FIGS. 4A and 4B, has an elongated central aperture 86 formed therein and is slightly curved to generally conform to the arcuate shape of the leaf spring 36. As shown in FIGS. 5A and 5B, the platen 44 has a bottom portion 90 and a top portion 92, the bottom portion 90 being wider than the top portion 92. The top portion 92 of the platen 44 is loosely disposed within the slot 43 (FIG. 4B) formed in the cassette 12 and is retained in the slot 43 only by the presence of the flexible tube 40 beneath the bottom of the platen 44, as shown in FIG. 4A.

Figure 6:
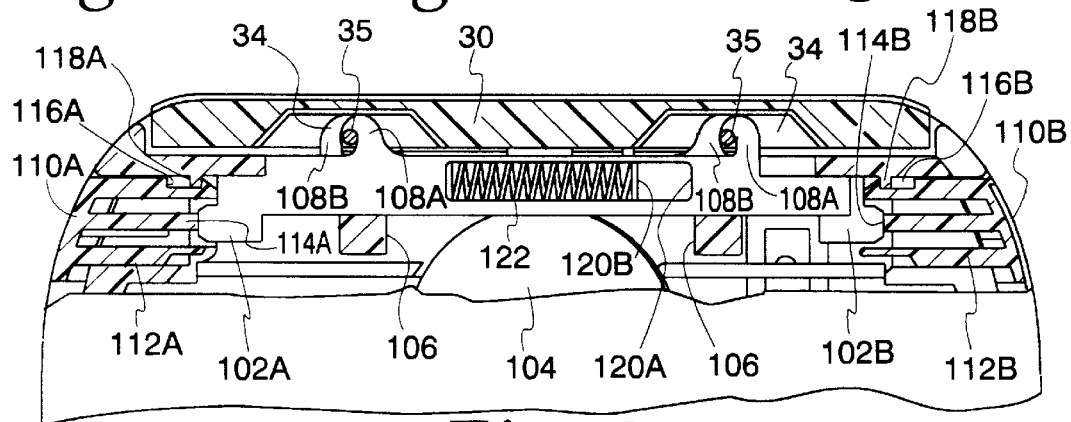
FIG. 6 is a cross-sectional side view of a portion of the infusion pump.

The infusion pump 10 has a latching mechanism 100, illustrated in FIG. 6, for retaining the door 30 in its closed position. Referring to FIG. 6, the latching mechanism 100 includes a pair of horizontally slidable metal plates 102a, 102b which are supported by a flat portion of a rotary pump wheel housing 104 and a pair of support beams 106. Each of the metal plates 102a, 102b has a respective pair of curved latch members 108a, 108b integrally formed therewith. A pair of independently operable door-release buttons 110a, 110b are disposed on either side of the infusion pump 10. Each door-release button 110a, 110b has a hollow cylindrical body portion 112a, 112b and a central member 114a, 114b disposed within the hollow body portion 112a, 112b. Each of the central members 114a, 114b engages a respective end of one of the slidable plates 102a, 102b. A pair of annular slots 116a, 116b are formed in the body portions 112a, 112b, and a pair of ridges 118a, 118b integrally formed with the pump housing are disposed within the slots 116a, 116b to limit the horizontal displacement of the door-release buttons 110a, 110b.

Each of the slidable plates 102a, 102b has a respective central aperture 120a, 120b disposed therein, and a spring 122 is disposed within both of the central apertures 120a, 120b so as to spring-bias or force each of the slidable plates 102a, 102b against the central member 114a, 114b of the door-release button 100a, 110b with which the end of the slidable plate 102a, 102b makes contact. The spring 122 may be retained within the apertures 120a, 120b by an L-shaped retaining member (not shown).

As shown in FIG. 6, the two curved latches 108a, 108b of each of the plates 102a, 102b engage both of the rods 35 fixed to the underside of the pump door 30, due to the force of the spring 122, thus preventing the door 30 from being opened. Each plate 102a, 102b alone is sufficient to keep the door 30 closed. To open the door 30, both of the door-release buttons 110a, 110b must be simultaneously depressed, in which case the slidable plates 102a, 102b are moved, against the force of the spring 122, to cause the curved latches 108a, 108b to disengage the metal rods 35, thus allowing the door 30 to be opened. The door 30 may be provided with a spring or other means (not shown) to cause the door 30 to open automatically when both of the door-release buttons 110a, 110b are pressed. Since both of the door-release buttons 110a, 110b must be actuated to open the door 30, any inadvertent opening of the door 30 due to the infusion pump 10 being dropped or jarred is reduced or eliminated.

Figure 7:
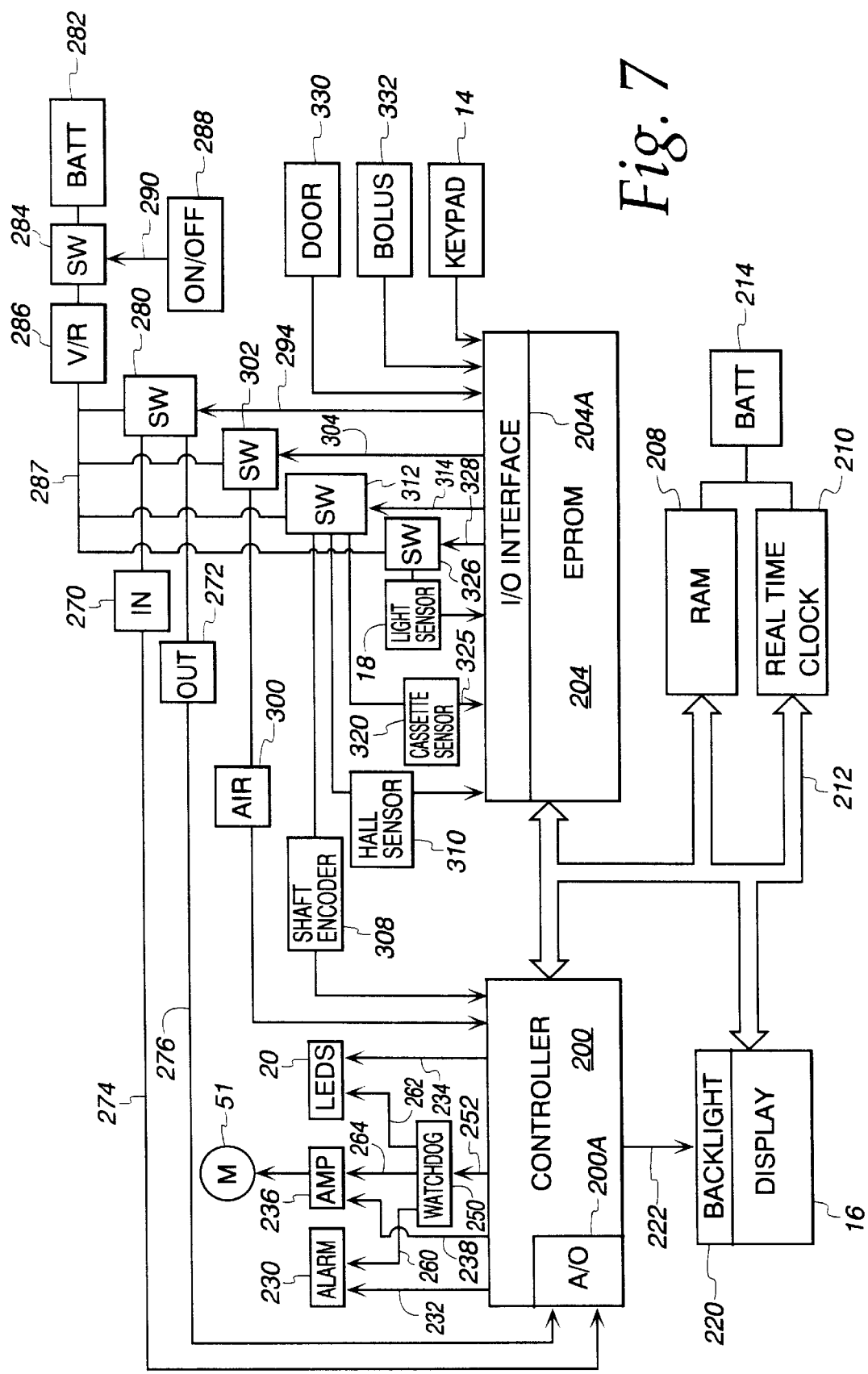
FIG. 7 is a block diagram of the electronic components of the infusion pump of FIG. 1.

A block diagram of the electronics of the infusion pump 10 is shown in FIG. 7. Referring to FIG. 7, the infusion pump 10 includes a controller 200 with a built-in analog-to-digital (A/D) converter 200a, an electrically programmable read-only memory (EPROM) 204 having a built-in input/output (I/O) interface 204a, a random-access memory (RAM) 208, a real-time clock 210 and the display 16, all of which are interconnected by a communications bus 212. The display 16 has a backlight 220 which is selectively activated by an enable signal generated on a line 222 interconnecting the controller 200 and the backlight 220. Both the RAM 208 and the real-time clock 210 are connected to a battery 214 which supplies power to them only in the absence of system power (generated by a second battery 282). Since it is always powered, the RAM 208 is a non-volatile memory.

The controller 200, which may be a conventional microcontroller such as an 80C196KB commercially available from Intel Corporation, controls an audible alarm generator 230 via a line 232, the LEDs 20 via a line 234, and an amplifier circuit 236 via a line 238. The amplifier circuit 236 is connected to drive the pump motor 51 which drives the rotary pump wheel 49. During normal operation, the controller 200 also sends a periodic signal to a conventional watchdog timer 250 via a line 252. If the controller 200 should fail to transmit the periodic signal to the watchdog timer 250, which would indicate failure or malfunction of the controller 200, the watchdog timer 250 transmits a signal via a line 260 to cause the alarm 230 to sound, transmits a signal via a line 262 to cause the red LED to be illuminated, and transmits a signal via a line 264 to the amplifier circuit 236 to cause the pump motor 51 to stop.

The pump 10 has a number of sensors which sense various conditions relating to the operation of the pump. These sensors include an input pressure sensor 270 for detecting the liquid pressure within the flexible tube 40 at a point upstream of the rotary pump wheel 49 and an output pressure sensor 272 for detecting the liquid pressure within the flexible tube 40 at a point downstream of the rotary pump wheel 49. The input pressure sensor 270 generates an analog signal, indicative of the input pressure, which is transmitted to the A/D converter 200a via a line 274, and the output pressure sensor 272 generates an analog signal, indicative of the output pressure, which is transmitted to the A/D converter 200a via a line 276. Each of the pressure sensors 270, 272, which detect occlusions with the flexible tube 40 or the tubing 52, 54 connected thereto, may be provided in the form of a strain gauge or beam (not show) which is in contact with the exterior of the flexible tube 40 and a high-gain amplifier (not shown) connected to the strain beam.

The pressure sensors 270, 272 are connected to and receive power from a power switch 280 which is connected to a battery 282 through a system power switch 284, a voltage regulator 286, and a system power line 287. The system power switch 284 selectively supplies power from the battery 282 to the voltage regulator 286 based on the state of a pump on/off switch 288 connected to the system power switch 284. The power switch 280 is controlled by the controller 200 via the bus 212, the I/O interface 204a, and a line 294 which interconnects the I/O interface 204a and the power switch 280.

The pump 10 has an air-in-line sensor 300, which may be provided in the form of a conventional piezoelectric transmitter and receiver (not shown) coupled to a sensing circuit (not shown), to detect the presence of any significant air bubbles within the flexible tube 40. The air-in-line sensor 300 receives power from a power switch 302 which is connected to the system power line 287 and controlled by the controller 200 via a line 304 connected to the I/O interface 204a.

The pump 10 has a shaft encoder sensor 308 and a Hall-effect sensor 310 which receive power from a power switch 312 coupled to the system power line 287 and controlled by the controller 200 via a line 314. The shaft encoder sensor 308, which is disposed on the shaft of the motor 51, may be a two-phase motion sensing encoder which provides two signal outputs to the controller 200. The rotational speed of the motor 51 and its direction of rotation are determined by the controller 200 based upon the rate and phase relationship between the two signal outputs. The Hall-effect sensor 310 is disposed adjacent the rotary pump wheel 49 and detects magnetic encoding on the pump wheel 49 for detecting rotation of the wheel 49.

Figure 8A:
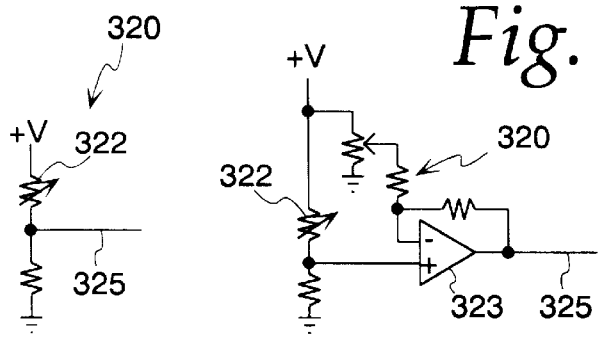
FIGS. 8A–8C illustrate various embodiments of the cassette sensor shown schematically in FIG. 7.
Figure 8B:
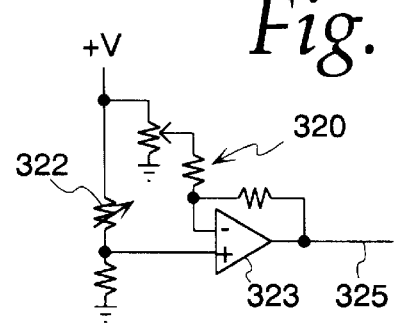
Figure 8C:
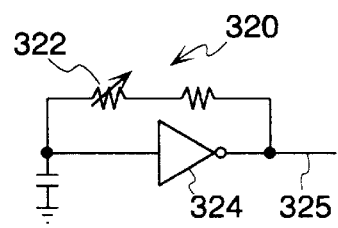

A cassette sensor 320, which is also connected to the power switch 312, detects the type of cassette which is inserted into the pump 10. As described below, the pump 10 may accept different types of cassettes and take different operating actions based upon the type of cassette which is inserted. Various possible embodiments of the cassette sensor 320 are shown in FIGS. 8A–8C. Each embodiment includes a force-sensitive resistive element 322 disposed in a sensing circuit. The circuits of FIGS. 8A and 8B act as force-to-voltage converters (the amplifier 323 in FIG. 8B is an operational amplifier), and the circuit of FIG. 8C (which includes a Schmidtt trigger 324) acts as a force-to-frequency converter.

The force is generated by the physical contact between the downwardly angled finger 82 of the second type of cassette 12 shown in FIGS. 3A and 3B and the force-sensitive resistive element 322 when the cassette 12 is inserted into the pump 12 and the door 30 is closed. Since the first type of cassette 12 shown in FIGS. 2A and 2B has no downwardly extending finger, the insertion of that type of cassette does not result in any physical contact with the force-sensitive resistive element 322. Thus, the resistance of the resistive element 322 changes only when the second type of cassette 12 is inserted, thus causing the cassette sensor 320 to generate an electrical signal (a voltage signal) in the cases of FIGS. 8A and 8B and a frequency signal in the case of FIG. 8C) indicative of the type of cassette inserted on a line 325 connected to the I/O interface 204a. The force-sensitive resistive element 322 is a conventional component which is commercially available from Interlink Electronics of Carpinteria, Calif. As described below, other types of sensors may be utilized.

Referring to FIG. 7, the ambient light sensor 18 is connected to a power switch 326 which is controlled by the controller 200 via a line 328 from the I/O interface 204a. Signals generated by a door-open sensor 330, a bolus infusion request switch 332, and the keypad 14 are transmitted to the controller 200 via the I/O interface 204a. Although not shown in FIG. 7 for purposes of simplicity, the controller 200, the EPROM 204, the RAM 208, and the display 16 are also connected to and receive power from the system power line 287.

Figure 9:
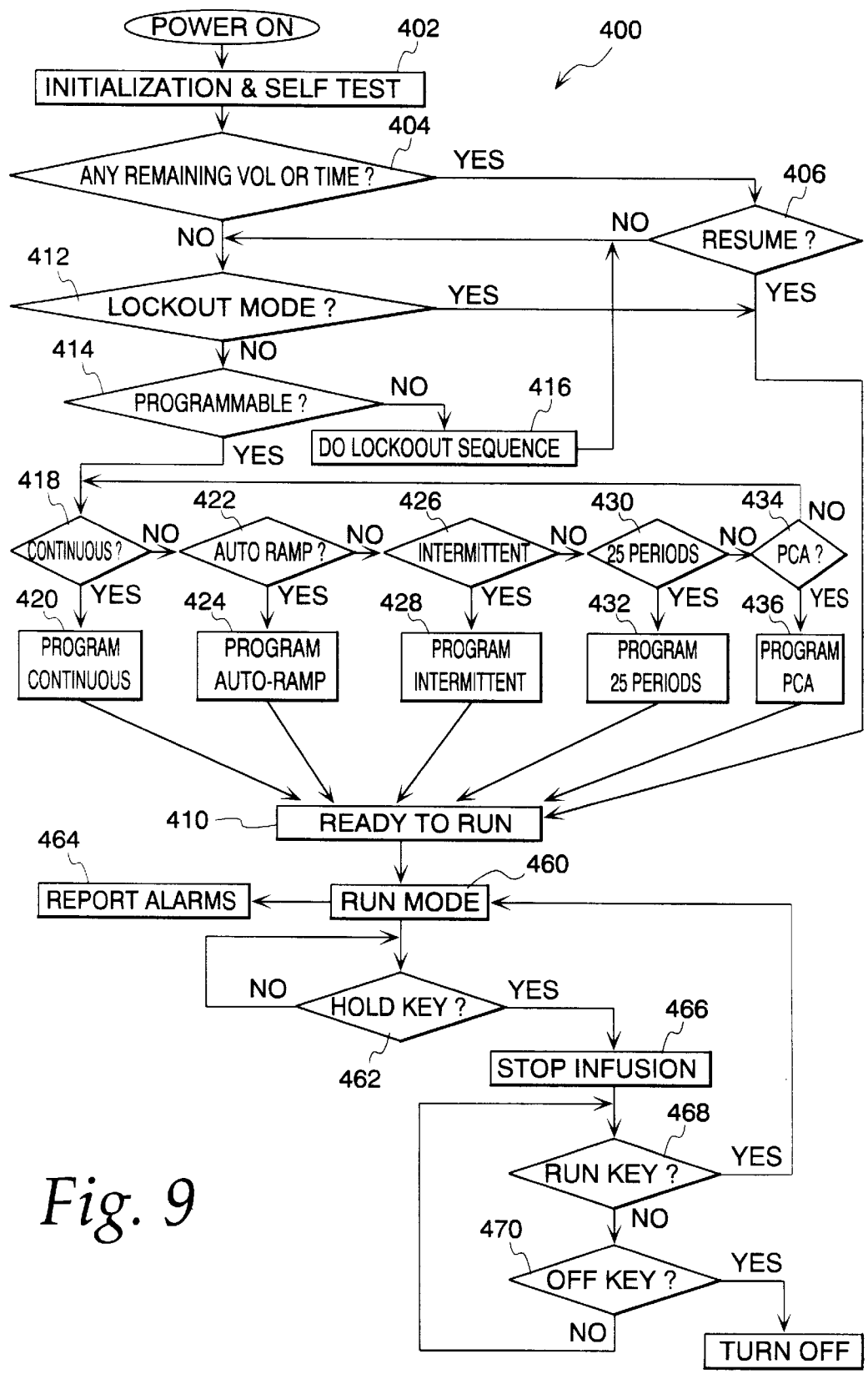
FIG. 9 is a flowchart of the overall operation of the infusion pump.

The operation of the infusion pump 10 is controlled by a computer program stored in the EPROM 204 and executed by the controller 200. A flowchart of the overall operation is illustrated in FIG. 9. Referring to FIG. 9, when the pump 10 is turned on via the on/off switch 288, at step 402 the pump is initialized and a test of the pump operation is performed. The pump 10 may be turned off temporarily during an infusion, in which case the pump 10 may continue the infusion when it is turned back on, as described below. At step 404, if there is any remaining volume of liquid to be infused by the pump or any additional time remaining for an infusion, which would be the case where the pump was temporarily turned off during an infusion, the program branches to step 406, where the user is asked, via a message displayed on the display 16, whether the previous infusion should be resumed. If the user answers yes (via the keyboard 14), the program branches to a ready-to-run step 410. If the previous infusion is not to be resumed, the program branches to step 412.

The infusion pump 10 has a lockout mode in which the user may be prevented from programming the infusion parameters, such as the volume to be infused or the rate of infusion. For example, the pump 10 could be programmed by a medical assistant to deliver a particular infusion having a particular flow profile, flow rate, and volume to be infused. After programming that infusion, the medical assistant could place the pump in lockout mode, which would prevent the patient from changing any of the infusion parameters. At step 412, if the pump 10 has been previously placed in lockout mode, the program branches directly to the ready-to-run step 410, bypassing all programming steps.

At step 412, if the pump is not in lockout mode, the program branches to step 414, at which point the program prompts the user, via the display 16, to input whether the patient should be allowed to program the pump during the subsequent infusion. If the pump is not to be programmable, the program branches to step 416 where a lockout sequence is performed by requesting the user to input which infusion modes should be locked out. If the pump is to be programmable by the patient, the program bypasses step 416.

The infusion pump 10 has five basic modes of infusion: 1) a continuous mode in which the pump delivers a single volume at a single rate; 2) an auto-ramp mode in which the pump delivers liquid at a rate that gradually increases to a threshold rate, stays constant at the threshold rate, and then gradually decreases; 3) an intermittent mode in which the pump delivers discrete liquid volumes spaced over relatively long periods of time, such as a liquid volume every three hours; 4) a custom mode in which the pump can be programmed to deliver a unique infusion rate during each of 25 different time periods; and 5) a pain-controlled analgesic (PCA) mode during which the pump will periodically infuse boluses of analgesic in response to periodic requests by the patient, which requests are made via the bolus-request key 332.

At step 418, the pump 10 generates on the display 16 the prompt "Continuous?" to the user. If the user desires to use the pump in its continuous mode, the user answers "yes" via the keypad 14, and the program branches to step 420 at which the continuous mode is programmed by the user by entering a number of infusion parameters, such as the desired infusion rate, the volume to be infused, etc. At step 418, if the user does not want to use the continuous mode, the user answers "No", and the program branches to step 422. Steps 422–436 are generally the same as steps 418 and 420, except that the user may be prompted for different infusion parameters, depending on which of the five possible infusion modes is selected.

Figure 10:
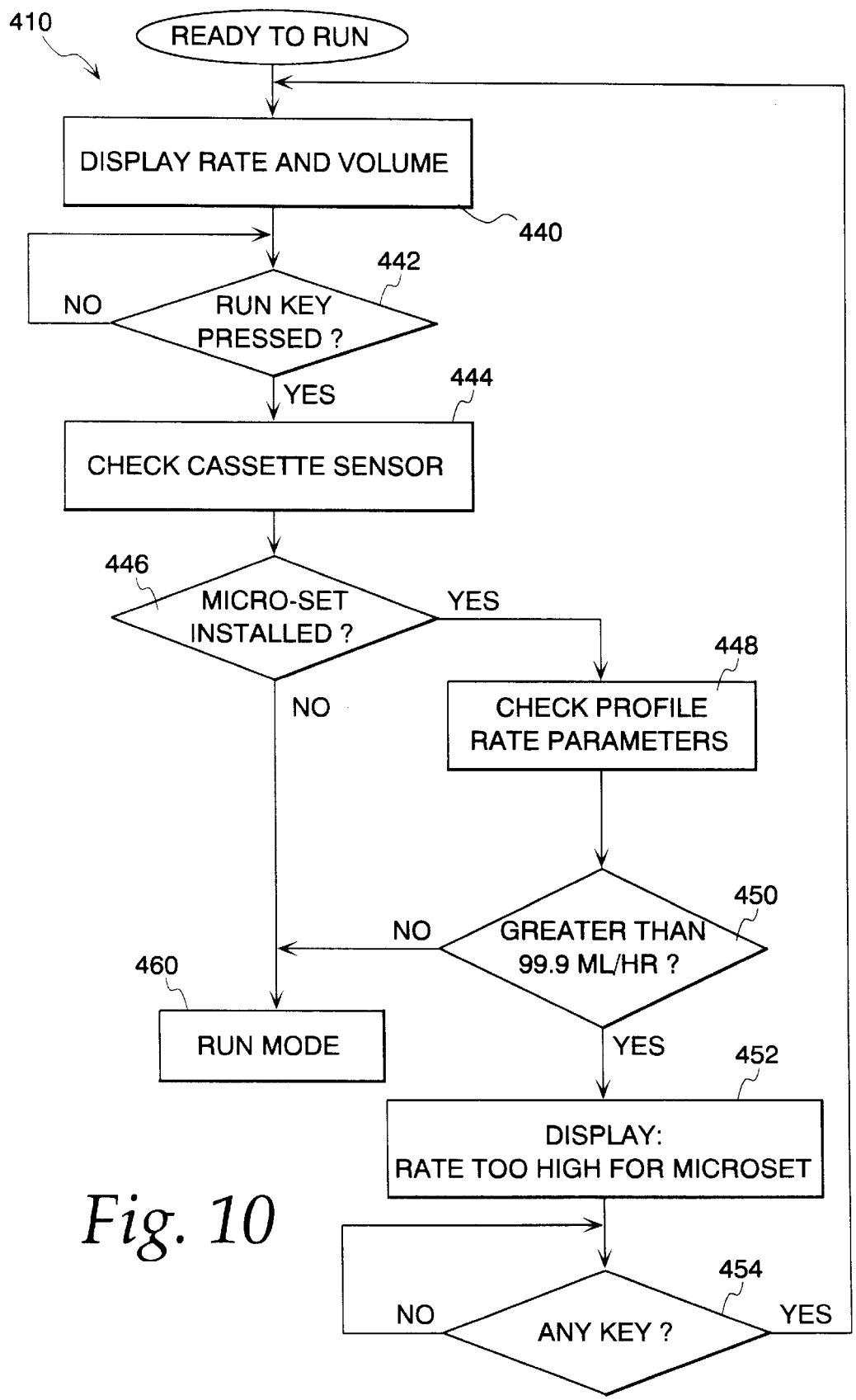
FIG. 10 is a flowchart of the ready-to-run step shown schematically in FIG. 9.

After the completion of one of the steps 420, 424, 428, 432, or 436, the program branches to the ready-to-run step 410, a flowchart of which is shown in FIG. 10. Referring to FIG. 10, the ready-to-run step 410 includes a step 440 at which the infusion rate and the volume to be infused which were entered during one of the programming steps 420, 424, 428, 432, 436, are shown on the display 16. Then the program waits at step 442 until the "Run" key of the keypad 14 is pressed, at which point the program branches to step 444 where the cassette sensor 320 is checked to determine which type of cassette has been inserted into the infusion pump 10.

The infusion pump 10 has the capability to alter its operation based upon the type of cassette 12 which is inserted into the pump 10, as determined by the cassette sensor 320. In one embodiment, the insertion of the cassette 12 shown in FIGS. 3A–3B, which is referred to herein as a "micro-set", prevents the infusion pump 10 from performing an infusion if the programmed infusion rate exceeds a predetermined limit. In this embodiment, at step 446, if a micro-set has been installed, the program branches to step 448 where the infusion rate parameters entered during one of the programming steps 420–436 are checked. At step 450, if the programmed infusion rate exceeds the predetermined limit, which may be 99.9 milliliters/hour, the program branches to step 452 where the pump generates a message on the display 16 to that effect and branches back to step 440 upon any key being pressed at step 454. If a micro-set was not installed as determined at step 446, the program skips steps 448–454 and branches directly to the run mode 460 shown in FIG. 9.

Referring back to FIG. 9, during the run mode 460, the pump 10 infuses the patient with a liquid medicant in accordance with the infusion mode selected at one of steps 418, 422, 426, 430, 434 and the infusion parameters entered at one of steps 420, 424, 428, 432, 436. The pump 10 remains in the run mode 460 until the hold key is pressed, as determined at step 462. Upon the occurrence of an alarm condition, an alarm is reported at step 464.

At step 462, if the hold key is pressed, the infusion is stopped at step 466, and the pump 10 waits for the run key to be pressed at step 468 or the on/off switch to be turned off at step 470.

Summarizing the operation described above, if the pump is to be utilized in lockout mode, a medical assistant turns the pump on, programs the desired infusion mode at one of steps 420, 424, 428, 432, 436, and then turns the pump off. The programmed infusion parameters will be retained in the nonvolatile memory 208. The medical assistant would then turn the pump back on, press the "No" key in response to the "Programmable?" prompt at step 414, enter the lockout information at step 416, and then turn the pump off again. When the patient subsequently turned on the pump to perform the infusion (after a cassette 12 is primed with the liquid to be infused and inserted into the pump), the program would proceed from step 412 directly to the ready-to-run step 410, which would prevent the patient from altering the infusion parameters.

If the lockout mode was not utilized, the medical assistant or the patient could turn the pump on, program the desired infusion mode, and then press the "Run" key to start the infusion without every turning the pump off.

The ability of the pump to take different actions based upon the type of cassette inserted into the pump could be utilized in many ways. For example, the pump could be utilized with any of four different types of cassettes, and the pump could be preprogrammed with a unique infusion mode and/or a unique set of infusion parameters for each type of cassette.

The different infusion modes could be based on the liquid medicant to be infused. For some liquid medicaments, it may be desirable to utilize the auto-ramp mode of infusion so as not to "shock" the patient by starting the infusion at a relatively large flow rate. These liquid medicaments would be used with a type of cassette that, when inserted into the pump, would cause the pump to automatically set the infusion mode to the auto-ramp mode. Thus, in this example, the program illustrated in FIG. 9 would branch from step 414 directly to step 424 without any intervening programming steps. For other liquid medicaments, the continuous mode of infusion may be appropriate. The infusion parameters entered at one of steps 420, 424, 428, 432, 436 could also be customized based upon the type of cassette inserted and/or the liquid medicant to be infused.

Different types of cassettes could be distinguished by the pump 10 based upon the length (or flexibility) of the flow-stop member (which could have four slightly different lengths or flexibilities), so that four distinct forces would be generated on the force-sensitive resistive element 322, or in a conventional manner based upon other structural features of the cassette.

For example, two light detectors could be disposed side by side in the top portion of the pump, each light detector having a transmitter which transmits a light beam to an associated receiver. Each cassette could be uniquely identified by the presence (or absence) of two notches, each notch being positioned adjacent one of the light detectors. Each light detector would detect the presence of a notch because the light beam would be uninterrupted when the cassette was inserted into the pump, whereas the absence of a notch would cause the light beam to be interrupted upon insertion of the cassette. Thus, the use of two light detectors and two associated notch locations would allow detection of four different types of cassettes, thus allowing four preprogrammed modes of pump operation.

Figure 11:
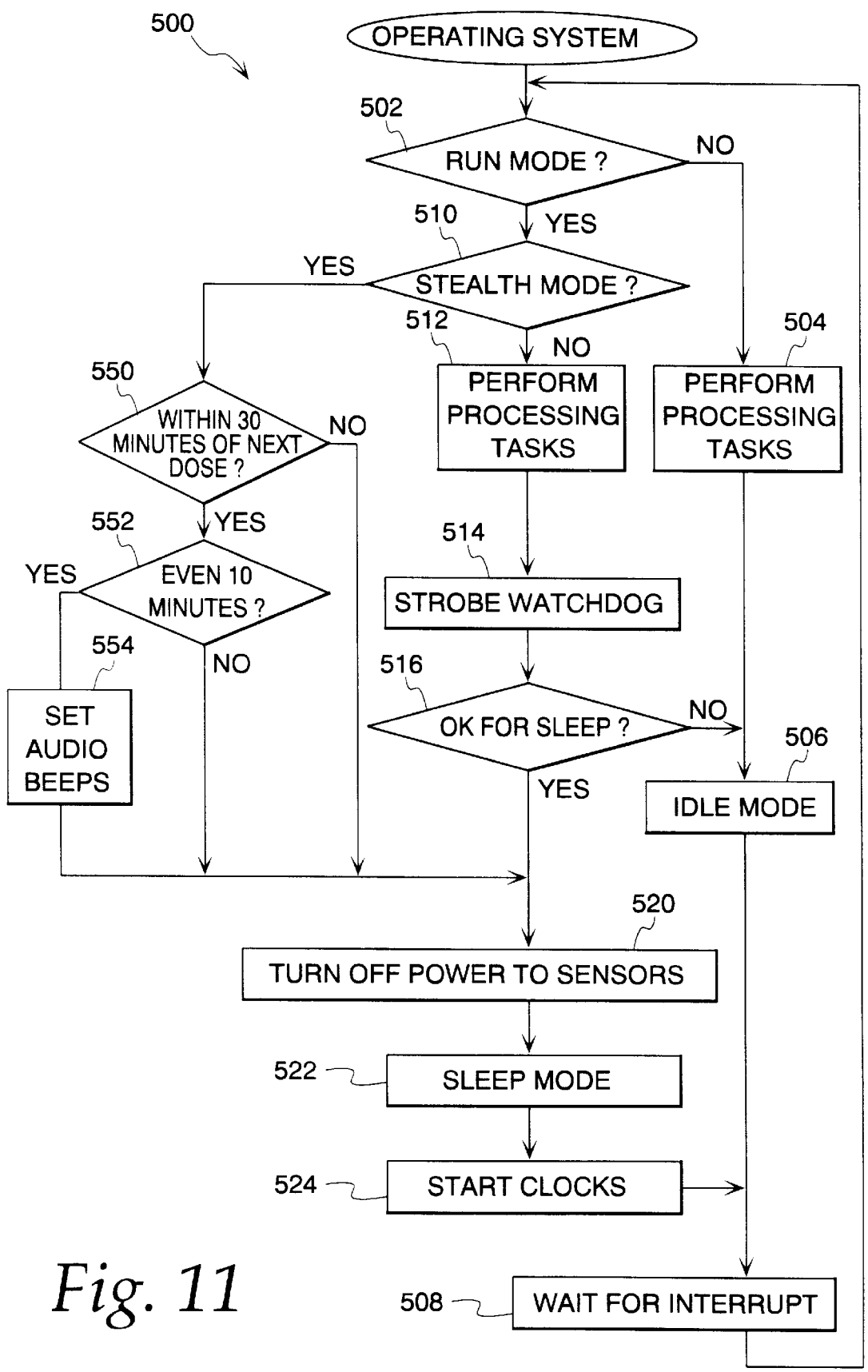
FIG. 11 is a flowchart of the operating system utilized by the infusion pump.

A flowchart of the operating system 500 of the infusion pump 10 is illustrated in FIG. 11. The operating system 500 determines how the operations and tasks shown in the flowchart of FIG. 9 are performed.

If the pump is in the run mode 460 shown in FIG. 9 and the pump is infusing at a relatively low flow rate, the pump may operate in a sleep mode which utilizes a relatively low rate of power consumption from the battery 282, such as 50 microamperes. When in the sleep mode, the controller 200 does not execute any instructions of the computer program, and its internal clocks are turned off. The pump is periodically placed in an idle mode which utilizes an intermediate rate of power consumption, such as 8 milliamperes. When the pump is in the idle mode, the controller 200 does not execute any instructions of the computer program, but its internal clocks continue to run. If the pump is in neither the sleep mode nor the idle mode, the computer program is executed and the internal clocks in the controller 200 run. In this operating mode, power is consumed at a relatively high rate, such as 17 milliamperes.

Referring to FIG. 11, if the pump is not operating in the run mode 460 as determined at step 502, the program branches to step 504 where any of the processing tasks of steps 402–436 of FIG. 9 may be performed. As described above, these tasks relate to the initial programming of the infusion pump 10 and are user-interactive. When there are no more of such tasks to be performed, for example, when the user has paused during the programming of the pump or has completed the pump programming, the program branches to step 506, where the controller 200 is placed in its idle mode, described above, via a software command. The controller 200 exits the idle mode upon the generation of an interrupt that is generated at step 508. The interrupt is periodically generated by the controller 200, for example, every 20 milliseconds.

Thus, when the pump is not in the run mode 460, the program cycles through steps 502–508 where it alternately performs at step 504 one or more of the processing tasks shown at steps 402–436 in FIG. 9 and is idled at step 506 to conserve battery power.

Under certain conditions, the pump may operate in the sleep mode described above. The pump may operate in the sleep mode when it is in the run mode 460 (FIG. 9) and is pumping below a relatively low infusion rate threshold, such as five milliliters/hour.

To deliver such a low infusion rate, the motor 51 is not activated continuously, but is instead turned on periodically (the motor 51 has a minimum rate at which it must be driven or else it will stall) to deliver a relatively small volume of liquid medicant, 50 microliters for example, and then is turned off. It is when the motor 51 is turned off when the controller 200 is placed in the sleep mode. When the programmed infusion rate is below the threshold, the frequency with which the motor turns on and off is determined by the programmed infusion rate. If the programmed infusion rate is above the threshold, the motor 51 will pump continuously.

Referring to FIG. 11, at step 510, if the pump is not in a stealth mode (described below), the program branches to step 512 where a number of processing tasks relating to the infusion may be performed. At step 514, the watchdog timer 250 is strobed, and at step 516 the program determines whether the controller 200 may be placed in the sleep mode. As described above, the controller 200 may be placed in the sleep mode if the infusion rate is less than a predetermined threshold rate. There are also other conditions which must be satisfied. For example, the motor 51 cannot be active, an audio beep (in response to a key being pressed, for example) cannot be active, no timed functions can be active (such as a timed LED illumination), the backlight 220 cannot be on, and the display 16 cannot be scrolling text. If these conditions are satisfied, the program branches to step 520 where the power to a number of sensors is turned off, and to step 522 where the controller 200 is placed in its sleep mode.

The controller 200 remains in the sleep mode until it is "awakened" by any of three occurrences: 1) any key being pressed, including the bolus-request key 332; 2) the watch-dog timer timing out; or 3) a one-second strobe generated by the real-time clock 210. In the absence of conditions 1) and 2), the controller 200 will be awakened every second by the strobe from the real-time clock 210. Upon being awakened, the internal clocks of the controller 200 are started at step 524, and the program branches to step 508 where it waits for the next 20 ms interrupt generated by the controller 200.

The infusion pump 10 also has a stealth mode relating to the intermittent infusion mode of FIG. 9. In this mode, the pump 10 delivers an infusion spaced at relatively large time intervals, such as minutes or hours. Between infusions, the pump is placed in a stealth mode in which the controller 200 is put to sleep.

Figure 12:
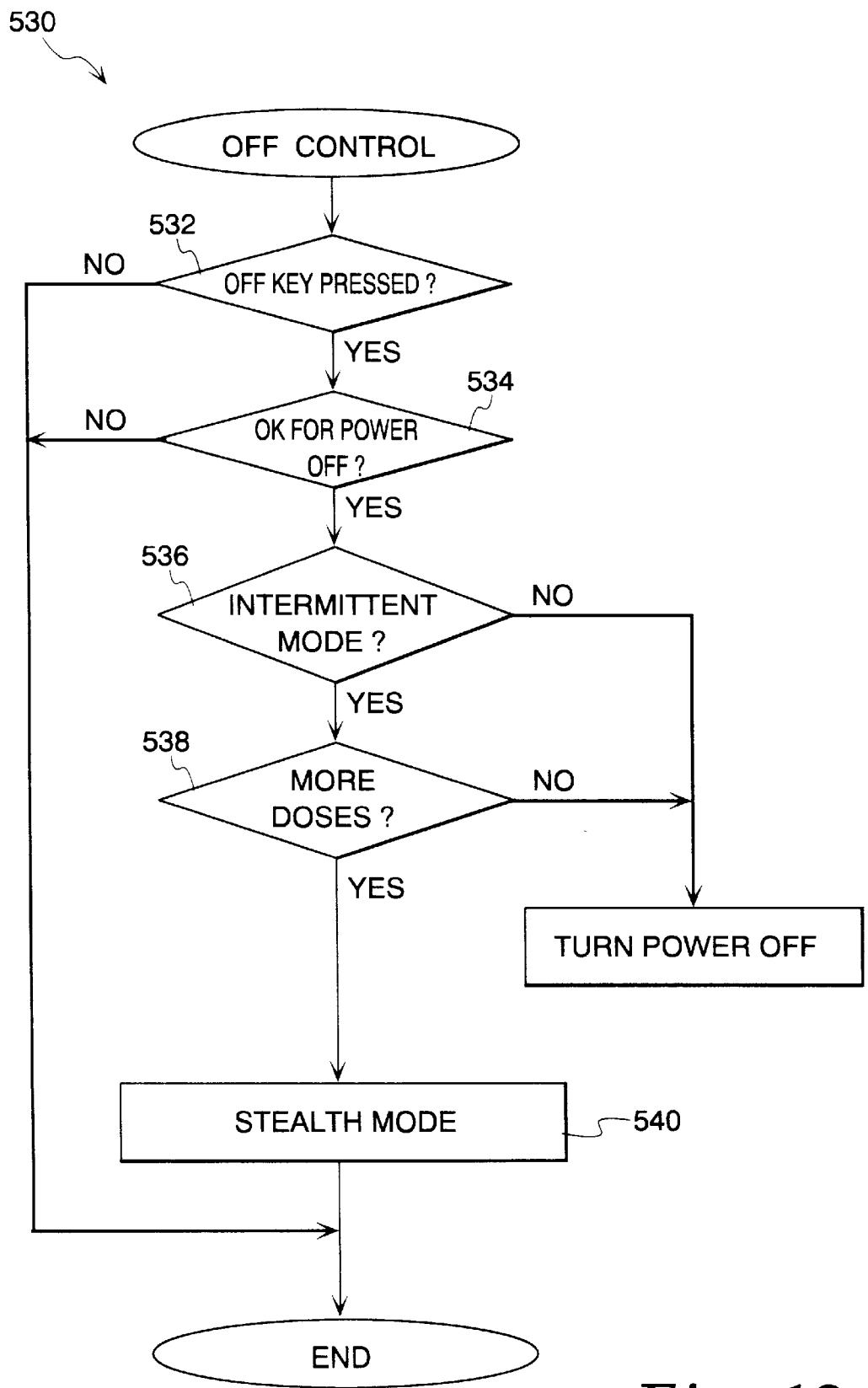
FIG. 12 is a flowchart of a turn-off routine performed during the operation of the infusion pump.

FIG. 12 illustrates an off-control routine 530 that is periodically invoked to determine whether the on/off switch 288 (FIG. 7) of the infusion pump 10 has been turned off. In that case, as determined at step 532, the program branches to step 534 where it determines if it is okay to turn the pump off (it is okay to turn the pump off as long as it is not in the run mode 460). If it is okay to turn the power off, the program branches to step 536. If the pump is not in the intermittent mode as determined at step 536, the power is turned off. If the pump is in the intermittent mode, the program branches to step 538, which determines whether there are any more periodic doses (infusions) to be made. If there are no more doses, the power is turned off.

If there is at least one additional dose, the pump is placed in the stealth mode at step 540. Referring back to step 510 of FIG. 11, if the pump is in the stealth mode, the program branches to step 550, which determines whether the next dose in the intermittent mode is scheduled within the next 30 minutes. If not, the program branches to steps 520–522 where the controller 200 is put to sleep.

If the next dose is within 30 minutes as determined at step 550, the program branches to step 552, where it determines whether the time until the next dose, or the time after that dose if not given, is a multiple of ten minutes. If it is, then the program branches to step 554, where the pump 10 generates an audible beep to the user as a reminder that the next dose is a multiple of ten minutes away. Thus, when the intermittent infusion mode is being used and the pump is in the stealth mode, the patient is given three audible warnings that the next dose is imminent, a first warning at 30 minutes prior to the dose, a second warning at 20 minutes prior to the dose, and a third warning at 10 minutes prior to the dose. If the next dose is not given on schedule, a fourth warning is generated at the time of the dose, and three additional warnings, spaced 10 minutes apart, are given after the time for the dose.

During the operation of the infusion pump 10, a number of the sensors used to sense various conditions may be turned on only when they are active in order to conserve battery power. The sensors that are selectively turned on include the input pressure sensor 270, the output pressure sensor 272, the air-in-line detector 300, the shaft encoder 308, the Hall-effect sensor 310 and the ambient light sensor 18. This powering of these sensors is controlled by a number of computer program routines, three of which are illustrated in FIGS. 13A–13C.

Figure 13A:
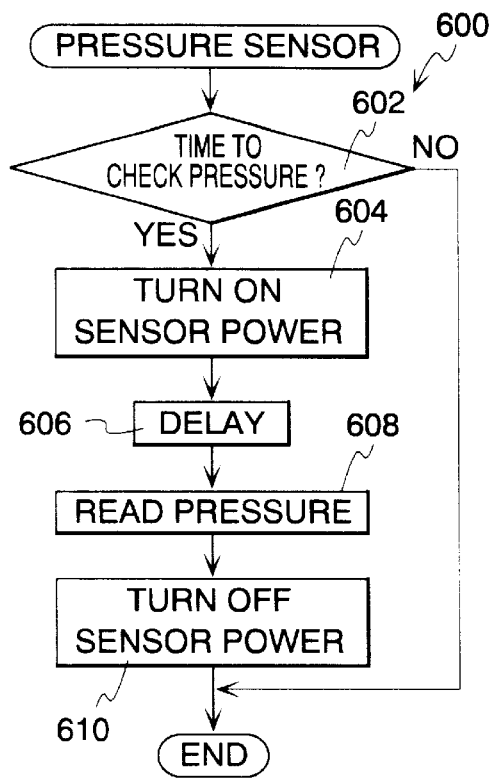
FIGS. 13A–13C are flowcharts of three sensor routines performed during the operation of the infusion pump.

Referring to FIG. 13A, a pressure sensor routine 600 may be used for the selective powering of the input and output pressure sensors 270, 272. If it is time to check either the input pressure or the output pressure in the flexible tube 40 as determined at step 602, the power supplied to both pressure sensors 270, 272 is turned on at step 604 via the line 294 to the power switch 280. The program then delays (e.g. a delay of 20 ms) at step 606 to allow the sensors 270, 272 to stabilize, and then the sensed pressure is read at step 608, following which both sensors 270, 272 are turned off at step 610 via the control line 294 to the power switch 280.

Figure 13B:
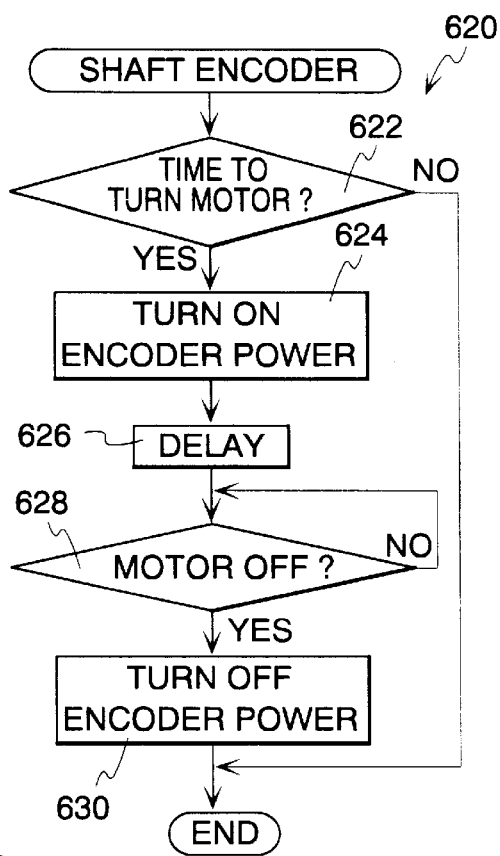

Referring to FIG. 13B, a sensor routine 620 may be used for the selective powering of the shaft encoder 308 of the motor 51. The shaft encoder 308 is active only when the motor 51 is turning, as determined at step 622. If it is time to turn the motor 51, the power supplied to the shaft encoder 308 is turned on at step 624 via the control line 314 to the power switch 312. The program then delays at step 626 to allow the shaft encoder 308 time to stabilize, after which time the shaft 308 will automatically generate signals indicative of the rotational rate and direction of the motor shaft. When the motor stops turning, as determined at step 628, the power to the shaft encoder 308 is turned off at step 630 via the control line 314 to the power switch 312.

Figure 13C:
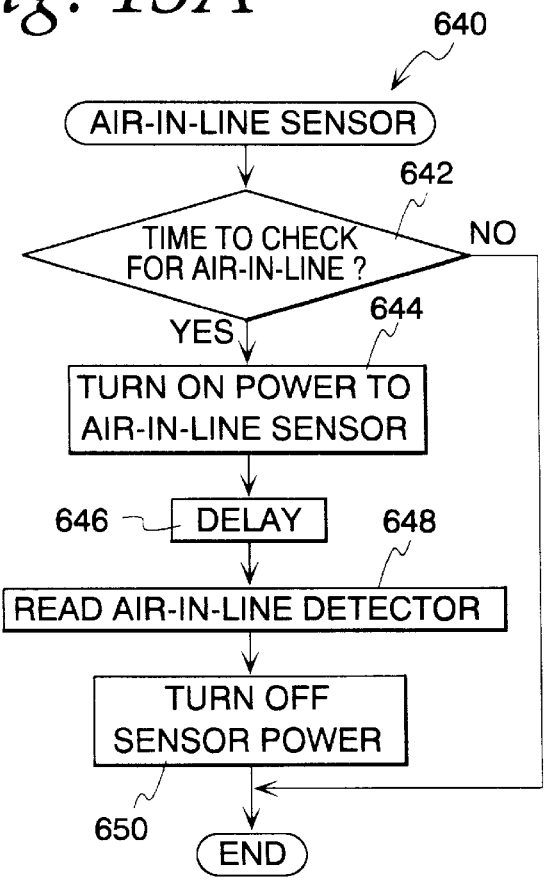

Referring to FIG. 13C, a sensor routine 640 may be used for the selective powering of the air-in-line sensor 300. If it is time to check the air-in-line sensor 300 as determined at step 642, the power supplied to the air-in-line sensor 300 is turned on at step 644 via the line 304 to the power switch 302. The program then delays (e.g. a delay of 2 ms) at step 646 to allow the sensor 300 to stabilize, and then the sensor 300 is read at step 648, following which the sensor 300 is turned off at step 650 via the control line 304 to the power switch 302. The routines shown in FIGS. 13B and 13C may be performed only when the criteria for the sleep mode are satisfied as described above in connection with step 516.

The infusion pump 10 incorporates another power-saving feature in that the backlight 220 for the display 16 is activated only under certain conditions. If either a key on the keypad 14 is pressed or a visual alarm message is generated on the display 16, the routine 700 causes the backlight 220 to be activated, via the control line 222, when the ambient light fails to surpass a predetermined threshold, as detected by the ambient light sensor 18.

Figure 14:
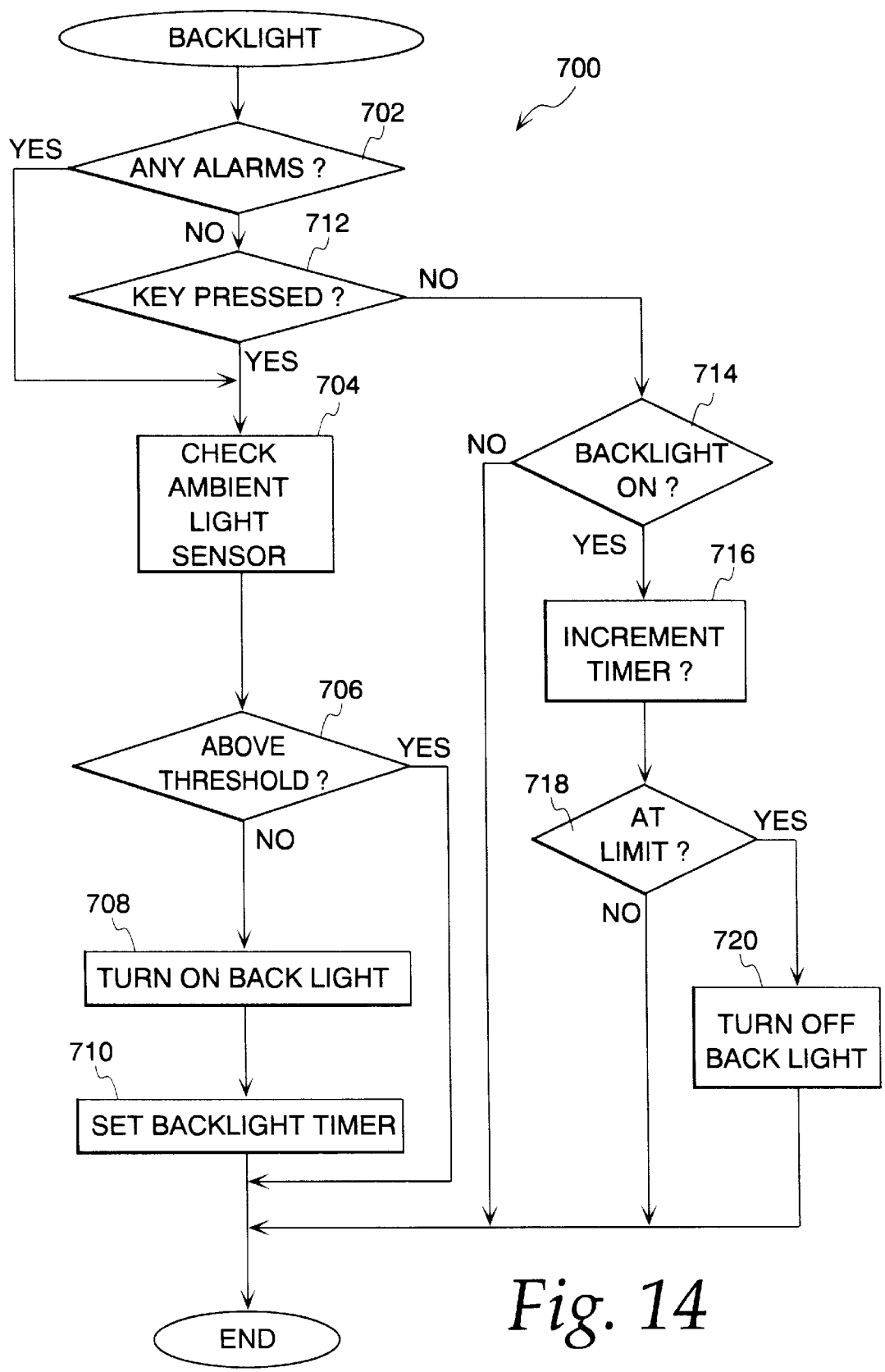
FIG. 14 is a flowchart of a backlight routine performed during the operation of the infusion pump.

Referring to FIG. 14, which is a flowchart of the backlight turn-on routine 700, if there is an alarm as determined at step 702, the program branches to step 704 where the ambient light sensor 18 is read (after the sensor 18 is powered up via the control line 328 connected to the power switch 326). If the amount of ambient light detected by the sensor 18 does not surpass a predetermined light threshold as determined at step 706, then the backlight 220 is turned on at step 708 via the control line 222 connected to the backlight 220. At step 710, a backlight timer, which causes the backlight 220 to be turned on only for a predetermined period of time, is then reset.

If no alarm was present as determined at step 702, then the program branches to step 712 which determines whether a key has been pressed. If so, then the program performs steps 704–710 to turn on the backlight 220 if the ambient light does not surpass a threshold level, as described above.

If no key has been pressed (and no alarm is present), the program branches to step 714. Steps 714–720 cause the backlight 220 to be automatically turned off after a predetermined period of time as determined by the backlight timer. At step 714, if the backlight is on, the program branches to step 716 where the backlight timer is incremented (the routine 700 is performed periodically, such as every 20 milliseconds). At step 718, if the backlight timer is at its limit, indicating that the predetermined period of time for which the backlight 220 should be illuminated has elapsed, then the program branches to step 720 where the backlight 220 is turned off.

During the programming and operation, the infusion pump 10 automatically records in the non-volatile memory 208 all significant infusion data to generate a complete historical data record which can be later retrieved from the memory 208 and used for various purposes, including clinical purposes to aid in determining how effective a particular infusion therapy was and treatment purposes to confirm that the prescribed infusion was actually delivered.

Figure 15:
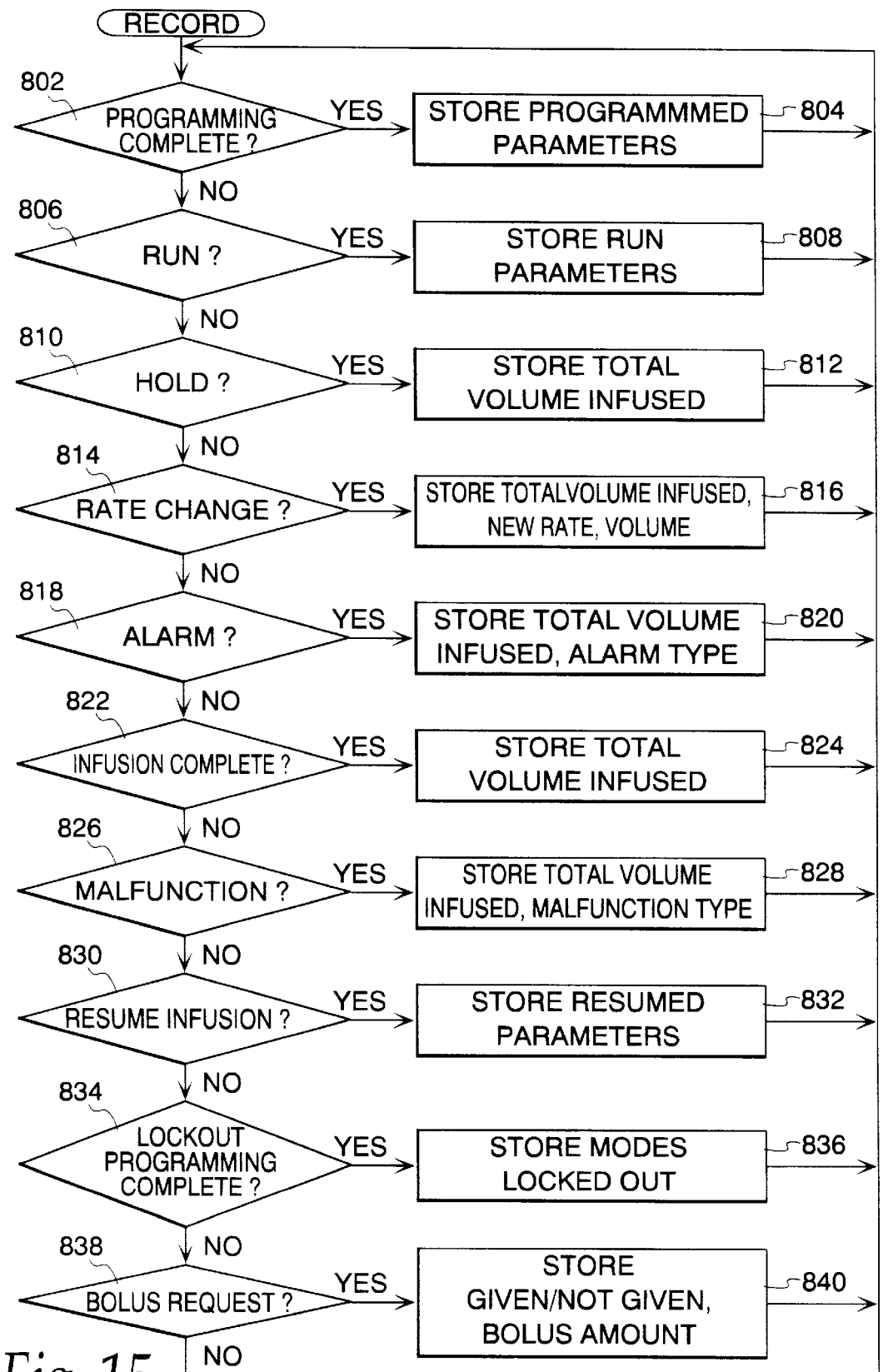
FIG. 15 illustrates a number of data-recording steps performed during the operation of the infusion pump.

FIG. 15 illustrates various steps at which infusion data is recorded that are performed during the overall pump operation shown generally in FIG. 9. The infusion data recorded in the memory 208 is set forth in Table 1 below. A number of events which trigger the storage of data are listed in the left-hand column of Table 1, and the infusion data that is recorded upon the occurrence of each event is listed in the right-hand column of Table 1. The time at which the infusion data is recorded, which is determined by the real-time clock 210, is also stored along with the infusion data.

TABLE 1

| EVENT | DATA RECORDED |
| --- | --- |
| Power On | Date and Time |
| Program | Infusion parameters. See Table 2. |
| Run | Infusion parameters. See Table 2. |
| Hold | Total Volume Infused |
| Restart | Time of Restart |
| Rate Changes | Total Volume Infused, Rate, Volume |
| Alarms | Total Volume Infused, Alarm Type |
| Infusion Complete | Total Volume Infused |
| Malfunctions | Total Volume Infused, Malfunction Type |
| Resume | Infusion parameters. See Table 2. |
| Maintenance Date | Date |
| Patient ID | Patient ID Number |
| Serial No. | Serial Number |
| Language Change | New Language |
| Lockout | Modes Locked Out |
| Pressure Select | New Pressure Setting |
| Bolus Request | Given/Not Given, Bolus Amount |
| Titration | New Parameters |
| Power Off | Time of Power Off |
| Version No. | Software Version Number |

Referring to Table 1 and FIG. 15, when the power to the infusion pump 10 is turned on, the date and time of the power turn-on is recorded. When the pump is completely programmed pursuant to one of steps 420, 424, 428, 432, 436 (FIG. 9) as determined at step 802, the programmed infusion parameters are stored at step 804, along with the time of such storage. The particular parameters that are stored depend upon which infusion mode was programmed. Several examples of infusion parameters that are stored for each of a number of infusion modes are illustrated in Table 2 set forth below.

TABLE 2

| INFUSION MODE | INFUSION PARAMETERS |
| --- | --- |
| Continuous | Infusion Mode |
| | Infusion Rate |
| | Volume To Be Infused |
| | Delay Time |
| | Total Bag Volume |
| | KVO Rate |
| Auto-Ramp | Infusion Mode |
| | Infusion Rate |
| | Volume To Be Infused |
| | Delay Time |
| | Total Bag Volume |

TABLE 2-continued

| INFUSION MODE | INFUSION PARAMETERS |
| --- | --- |
| | Duration of Up-Ramp |
| | Duration of Down-Ramp |
| | KVO Rate |
| Intermittent | Infusion Mode |
| | Total Infusion Time |
| | Number of Doses |
| | Dose Time |
| | Dose Volume |
| | KVO Rate |

When the pump enters the run mode 460 (FIG. 9) as determined at step 806, the time at which the run mode was begun, along with the parameters pursuant to which the infusion is performed, are stored at step 808.

At step 810, if the hold key is pressed, then the time at which the hold key was pressed along with the total volume infused at the time the hold key was pressed are stored at step 812. The pump also stores any infusion rate changes, such as changes caused by switching from a continuous rate to a keep-vein-open (KVO) rate, or in the intermediate mode, changing from a KVO rate to a higher infusion rate, the presence of which are detected at step 814. The new rate and the time at which the new rate started are stored at step 816.

At step 818, if any alarms are generated, the alarm type, the time at which the alarm occurred, and the total volume infused at the time of the alarm are recorded at step 820. If the infusion is completed as determined at step 822, the program branches to step 824 where the time at which the infusion was completed is stored along with the total volume infused. At step 826, if there is a malfunction, the malfunction type, the time at which the malfunction occurred, and the total volume infused at the time of the malfunction are recorded at step 828.

At step 830, if the infusion is resumed (when the pump is turned back on after having been turned off during an infusion), the time at which the infusion is resumed along with the infusion parameters are stored at step 832. Upon the completion of the programming of a lockout sequence as determined at step 834 (i.e., after step 416 of FIG. 9), the time at which the programming of the lockout was completed, is stored along with the infusion modes that were locked out. At step 838, upon the detection of a bolus request (via the bolus-request key 332 in FIG. 7), the time at which the bolus was requested is stored, along with an indication whether the bolus was actually given and the amount of the bolus.

Figure 16:
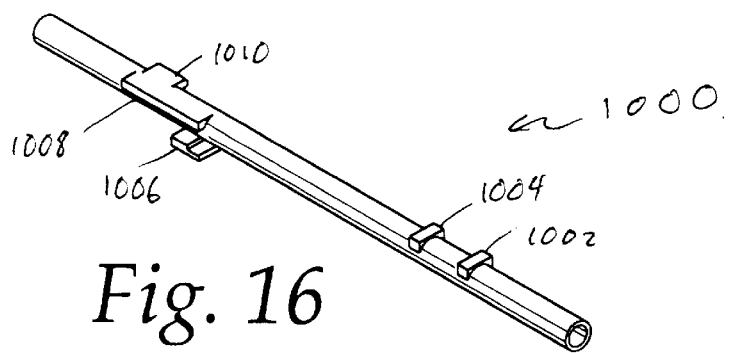
FIG. 16 is a perspective view of the unitary molded elastomer conduit for use with the medical infusion pump in accordance with the present invention.

Turning now to FIG. 16, the unitary molded elastomer conduit 1000 is shown in perspective view. The conduit 1000 is provided for fluid transport, having several elongated tubular sections integral with the molded conduit for facilitating the pump chamber, clamping, fluid transport characterization, and the like, for use with a medical infusion pump. FIG. 16 shows several external features molded on the outside of the conduit 1000. Particularly, positioning features 1002 and 1004 are used to align the conduit 1000 in the cassette 12 for positioning relative to the ultrasonic piezoelectric transmitter and receiver of the air-in-line sensor 300 which is used to detect presence of any significant air bubbles within the conduit 1000 at region 1014 (see FIG. 17) facilitating characterization of the fluid transport. Thus, self-registering features are provided to improve manufacturability and accuracy in placement of the conduit 1000 in the cassette 12.

External features are also provided on the conduit 1000 to facilitate the clamping function of the free flow clamp, particularly external features 1006 and 1008, and positioning feature 1010 may be positioned at the free flow clamp 60 as discussed above to facilitate clamping off of the lumen defined through the conduit 1000. As will be discussed further below, the molded conduit 1000 includes a plurality of integral elongated tubular sections (discussed in connection with FIG. 18) which define the continuous lumen through the conduit 1000 for medicament delivery by fluid transport therethrough. At least a first interior surface of the conduit 1000 is associated with one of the plurality of elongated tubular sections, and includes a first interior region for clamping off the lumen. Additionally, at least a second interior surface of the conduit 1000 is associated with another of the plurality of tubular sections, and includes a second interior region for coupling a signal across the conduit traversed to the lumen to characterize the fluid transport. The second interior region has a textured surface relative to the first interior region for controlling the energy from the signal coupled across the conduit traversed to the lumen. The textured surface effects the propagation of signals, e.g., ultrasonic energy being coupled into and through the conduit 1000 at region 1014. Clamping off of the lumen of the conduit 1000, as discussed in connection with at least the first interior surface at region 1016, facilitates clamping with the free flow clamp, e.g., features 1010 and 1006 facilitate the clamping of the lumen and also facilitate the use of an interior surface texture appropriate for the peristaltic pumping mechanism providing sufficient clamping pressure during the pumping to ensure accuracy of the swept volume of fluid medicament delivered with the peristaltic pump.

Figure 17:
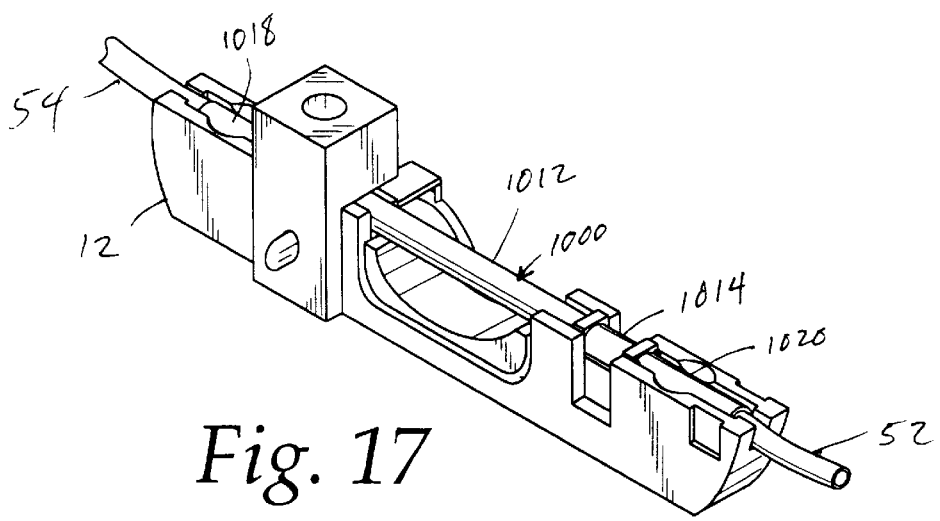
FIG. 17 illustrates the elastomer conduit of FIG. 16 positioned within a medical infusion pump cassette module.

FIG. 17 shows the conduit 1000 positioned in the cassette 12. As shown in FIG. 17, a region 1012 is positioned for receiving the peristaltic pumping mechanism of the medical infusion pump. Features 1004, 1006, and 1010 constrain and lock the region 1012 with the pumping area. A region 1014, as discussed, is positioned in the cassette 12 for use with the air-in-line sensor 300. Additionally, regions 1018 and 1020 of the conduit 1000 provide openings in the cassette 12 for use with a strain gauge or beam which is in contact with the exterior of the conduit 1000 at reference numerals 1018 and 1020 respectively, allowing the cantilever strain gauge or beam to determine upstream and down-stream occlusion characteristics of the fluid transport through the lumen of the conduit 1000. Tubing 52 and 54, as discussed above, are coupled to the conduit 1000 at the end regions, which end regions include a stepped opening for receiving the tubing 52 and 54 respectively at reference numerals 1022 and 1024 providing a registered fit between the conduit 1000 and the tubing 52 and 54 (see FIG. 18).

Figure 18:
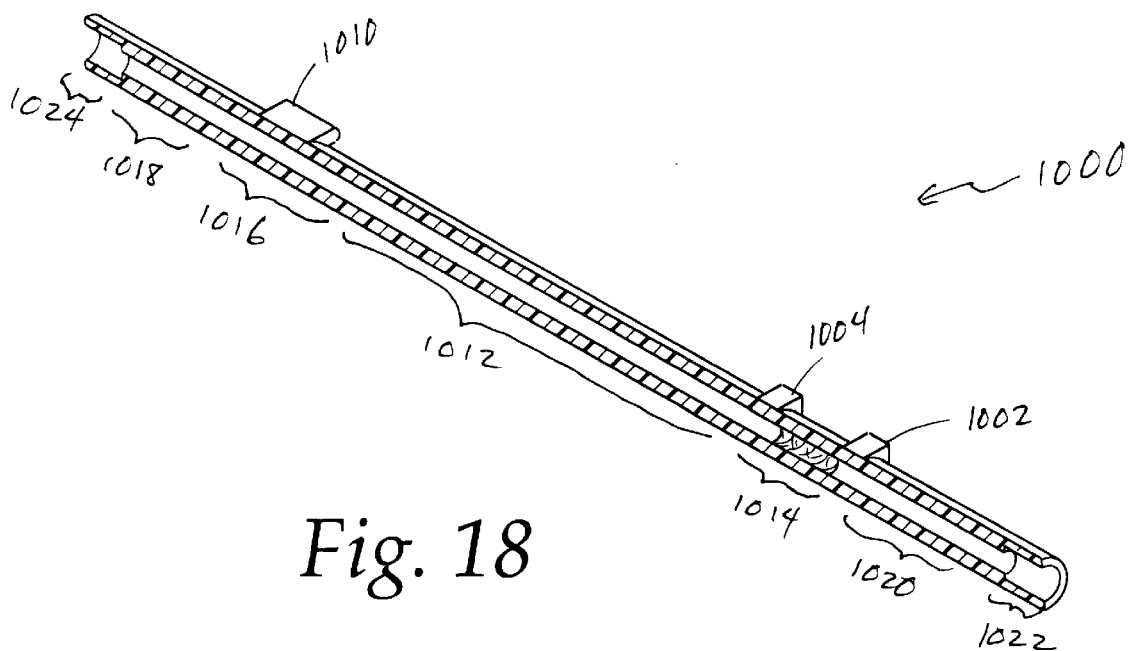

FIG. 18 shows the conduit 1000 in cross section with several elongated tubular sections defining the continuous lumen through the conduit 1000 shown as being formed integrally with the unitary molded elastomer conduit. The unitary elastomer conduit of the preferred embodiment is injection molded on a core pin using silicone compound in a pyrogen free environment. Silicone has desirable features including a relatively constant storage modulus or stiffness, and dynamic mechanical analysis characteristics over temperature with minimal volume drift superior to most conventional elastomers such as polyurethane or plasticized polyvinylchloride (PVC). Through the use of an elastomer such as a silicone, as opposed to a thermoplastic, the liquid injection molding over the core pin provides for accurate and repeatable manufacture of the several internal and external features of the conduit 1000.

As shown in FIG. 18, the region 1012 may be received by the peristaltic pumping mechanism of the medical infusion pump, which region includes an interior surface texture of sufficient coarseness to prevent sticking of the silicone tube to provide adequate clamping off of the region 1012 during peristaltic pumping operation to maintain clamping pressure during drug delivery as a swept volume of medicament flows through the conduit 1000 by way of the peristaltic mechanism of the medical infusion pump. Additionally, the region 1012 is molded to ensure a predetermined and reproducible volume therein to maintain a high degree of accuracy, e.g., plus/minus one percent, with the molded conduit 1000. The region 1014 provides a tubular section which when positioned within the medical infusion pump at the air-in-line sensors provides sufficient coupling of the ultrasonic signal from its smooth outer surface through the knurled textured portion, as discussed below, for sufficient ultrasonic energy transfer through the conduit 1000 traversed to the lumen for determining the presence of air in line with the fluid medicament. The knurled interior features provide enhanced scattering at the air/wall interface to better differentiate between air and water or other fluids. Additionally, the external features provided at a region 1016 facilitate the pinch-off of the lumen. As discussed above, the region 1016 provides for a clamping action used with the free flow clamp of the cassette 12. Regions 1018 and 1020 are used with the occlusion testing as discussed above, and regions 1022 and 1024 have stepped internal features at the ends of the conduit 1000 for receiving the tubes 52 and 54 coupling the fluid medicament to the cassette module of the peristaltic pump.

FIG. 19 is a cross-sectional view of the conduit 1000, identifying particularly the regions 1012, 1014, and 1016 which are shown in cross section in FIGS. 20–22. In FIG. 20, the region 1016 is shown as having an exterior surface 1028 and a somewhat coarse interior surface 1026 where the interior surface 1026 is provided as having an N4 surface texture. The designation N4 for the roughness specification of the interior surface denotes that the roughness is in metric units and that the root-mean-squared surface roughness should not exceed 4 micrometers. The N4 roughness is sufficient to yield sufficient hold pressure to clamp off the lumen under the operation of the flow clamp, in this area, where a displaced volume is not as much an issue as would be the case in region 1012 as shown in FIG. 21. The region 1012 in FIG. 21 provides an interior surface 1030 and external surface 1032. The interior surface at FIG. 21 is provided as having surface texture of 220 grit cross-hatched, honed to yield sufficient hold pressure to clamp-off the lumen during pump operation. In the current embodiment, the textures of the interior surfaces 1026 and 1030 are identical. The region 1014 is shown in cross section in FIG. 22 with a knurled interior region 1034 and a smooth external region 1036, providing textured surfaces particularly suited for ultrasonic signal energy transfer through the region 1014. The interior surface texture at 1034 and the exterior surface texture at 1036 are provided in the described embodiment for the use of ultrasonic detection of air-in-line conditions to characterize the fluid flow through the lumen. In particular, the smooth surface 1036 facilitates coupling of the ultrasonic signal into the region 1014 even in the presence of fluids external to the conduit 1000, so as to assure that an accurate assessment of the air-in-line detection is provided in such conditions. Additionally, the knurled interior surface texture 1034 facilitates scattering within an anechoic chamber structure for the ultrasonic signal propagating across the lumen of the conduit 1000. The degree of this scattering is dependent upon the relative impedances of the conduit and the contents within the lumen of the conduit 1000. Thus the matching of the signal transmission into and through the conduit 1000 allows for illumination with a sufficient signal to noise ratio (SNR) which facilitates the accurate amplitude detection of the signal at the air-in-line sensor 300.

Modifications and alternative embodiments of the invention will be apparent to those skilled in the art in view of the foregoing description. This description is illustrative only, and the invention is defined by the appended claims.

What is claimed is:

1. A unitary molded elastomer conduit for fluid transport, the conduit comprising:
   a plurality of elongated tubular sections defining a continuous lumen therethrough;
   a first interior surface of the conduit associated with one of the plurality of elongated tubular sections comprising a first interior region for clamping off said lumen; and
   a second interior surface of the conduit associated with another of the plurality of elongated tubular sections comprising a second interior region for coupling an ultrasonic energy signal across the conduit transverse to the lumen to characterize the fluid transport said second interior region having a textured surface relative to said first interior region effecting the propagation of the transmission of the signal energy from the signal coupled across the conduit transverse to the lumen thus enhancing the discrimination of entrained air detection.

2. A conduit as recited in claim 1 wherein said second interior surface is textured relative to said first interior region for impedance-dependent transmission of the signal energy.

3. A conduit as recited in claim 1 comprising a third interior surface of the conduit associated with another of the plurality of elongated tubular sections comprising a third interior region for receiving a peristaltic pumping mechanism for constraining a pumping area of the conduit.

4. A conduit as recited in claim 1 wherein said second interior surface is knurled relative to said first interior surface.

5. A conduit as recited in claim 1 wherein said plurality of elongated tubular sections are injection molded over a core pin to form the unitary molded elastomer conduit.

6. A conduit as recited in claim 1 wherein the elastomer comprises a pyrogen free silicone compound.

7. A conduit as recited in claim 1 comprising an exterior surface relative to said second interior surface of the conduit associated with the elongated tubular section, the exterior surface for coupling the signal across the conduit transverse to the lumen.

8. A conduit as recited in claim 7 wherein said second interior surface and said exterior surface of the conduit are provided for coupling ultrasonic energy transverse to the lumen to characterize the fluid transport.

9. A conduit as recited in claim 8 wherein said exterior surface relative to said second interior surface of the conduit associated with the plurality of elongated tubular sections is smooth relative to the exterior surfaces of others of the associated plurality of elongated tubular sections, the relatively smooth exterior surface being provided for improving the acoustic transmission of the signal across the conduit.

10. A conduit as recited in claim 1 comprising one or more external features for positioning said plurality of elongated tubular sections of the conduit for fluid transport and characterization.

11. A conduit as recited in claim 10 wherein said one or more external features comprise different thicknesses for closing the tubular section to facilitate clamping off of the lumen of the conduit.

12. A method of making a unitary molded elastomer conduit for use with a medical infusion pump, the conduit comprising:
    providing a plurality of elongated tubular sections defining a continuous lumen therethrough;
    molding a first interior surface of the conduit associated with one of the plurality of elongated tubular sections comprising a first interior region for clamping off said lumen;
    molding a second interior surface of the conduit associated with another of the plurality of elongated tubular sections comprising a second interior region for coupling a signal across the conduit transverse to the lumen to characterize the fluid transport, said second interior region having a textured surface relative to said first interior region directing the signal energy from the signal coupled across the conduit transverse to the lumen; and
    said first interior region and its associated elongated tubular section being positioned relative to the peristaltic pumping mechanism of the medical infusion pump.

13. A method as recited in claim 12 comprising the step of molding a third interior surface of the conduit associated with another of the plurality of elongated tubular sections for providing a pumping area which receives a peristaltic mechanism on the conduit.

14. A method as recited in claim 12 comprising the step of texturing the surface of the second interior region for providing impedance-dependent transmission of the energy from the signal coupled across the conduit traverse to the lumen for enhancing the discrimination of entrained air detection.

15. A method as recited in claim 12 comprising the step of clamping the lumen by providing an external force at external features on the molded second interior surface.

16. A method as recited in claim 12 wherein said providing step comprises forming a plurality of elongated tubular sections having one or more external features receivable in a cassette which is insertable into the medical infusion pump.

17. A method as recited in claim 16 wherein said external features are molded for positioning the plurality of elongated tubular sections of the conduit at predetermined locations of the cassette relative to the peristaltic pumping mechanism of the medical infusion pump.

18. A method as recited in claim 17 comprising the steps of providing external features for self positioning of the conduit.

19. A method as recited in claim 18 wherein the providing of the external features prevents moving of the conduit during pumping cycles.

20. A method as recited in claim 17 wherein said external features are molded with an outer collar or ring on the outside of the conduit for positioning relative to the peristaltic pumping mechanism of the medical infusion pump.

21. A method as recited in claim 20 comprising the step of providing an inner collar to position the interior conduit for registration with coupled tubing.

22. A method as recited in claim 20 wherein said external features provide for registration of at least said first interior region and the associated elongated tubular section relative to the peristaltic pumping mechanism of the medical infusion pump.

23. A method as recited in claim 20 wherein said external features prevent the conduit from twisting inside said cassette to maintain a uniform storage modulus for the conduit inside said cassette.

24. A method of infusing a medicament with a medical infusion pump, the method comprising the steps of:

molding a unitary elastomer conduit having a plurality of tubular sections defining a continuous lumen therethrough;

securing the conduit in a cassette for being received by the medical infusion pump;

providing a first interior surface of the conduit associated with one of the plurality of elongated tubular sections with a first interior region for clamping off the lumen;

providing a second interior surface of the conduit associated with another of the plurality of elongated tubular sections with a second interior region for coupling a signal across the conduit traversed to the lumen to characterize fluid transport;

texturing the surface relative to the first interior region to facilitate the transmission of the signal coupled across the conduit traversed to the lumen; and receiving a liquid medicament at the conduit, the first interior region and the associated tubular section being positioned relative to the peristaltic pumping mechanism of the medical infusion pump for fluid transport through the continuous lumen defined by the plurality of elongated tubular sections of the conduit.

25. A method as recited in claim 24 comprising the step of providing molded features on the outside of the conduit for locating the plurality of elongated tubular sections of the conduit within the cassette.

26. A method as recited in claim 24 providing a smooth external surface relative to the second interior region having the textured interior surface to direct the signal energy from the signal coupled across the conduit traversed to the lumen.

27. A method as recited in claim 26 comprising the step of providing an ultrasonic signal at the second interior region for coupling across the conduit traversed to the lumen to characterize the fluid transport.

28. A method as recited in claim 27 comprising the step of providing a coarse interior surface of the conduit to prevent sticking of the surface while facilitating pumping therethrough.

29. A medical infusion pump comprising:

a pump chamber cassette conduit comprising a plurality of elongated tubular sections defining a continuous lumen therethrough;

a first interior surface of the conduit associated with one of the plurality of elongated tubular sections comprising a first interior region for clamping off said lumen; and a second interior surface of the conduit associated with another of the plurality of elongated tubular sections comprising a second interior region for coupling a signal across the conduit transverse to the lumen to characterize the fluid transport, said second interior region having a textured surface relative to said first interior region directing the signal energy from the signal coupled across the conduit transverse to the lumen;

a tube for receiving a liquid medicament at the conduit, the first interior region and the associated tubular section being positioned relative to the peristaltic pumping mechanism of the medical infusion pump for fluid transport through the continuous lumen defined by the plurality of elongated tubular sections of the conduit; and a peristaltic pump mechanism for transporting the liquid medicament across the conduit of the pump chamber cassette.

30. A medical infusion pump as recited in claim 29 wherein said conduit comprises one or more external features for positioning the plurality of elongated tubular sections of the conduit in the pump chamber cassette for fluid transport by the pump.

\* \* \* \* \*